(12) United States Patent
Peters

(10) Patent No.: US 9,743,673 B1
(45) Date of Patent: Aug. 29, 2017

(54) MODIFICATION OF NITROGEN-FIXING RHIZOBACTERIA TO ENHANCE NODULATED PLANT RESISTANCE

(71) Applicant: IOWA STATE UNIVERSITY RESEARCH FOUNDATION, INC., Ames, IA (US)

(72) Inventor: Reuben John Peters, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 14/712,430

(22) Filed: May 14, 2015

Related U.S. Application Data

(60) Provisional application No. 61/996,674, filed on May 14, 2014.

(51) Int. Cl.
*C12N 1/20* (2006.01)
*A01N 63/00* (2006.01)

(52) U.S. Cl.
CPC .................................... *A01N 63/00* (2013.01)

(58) Field of Classification Search
CPC ................................ C12P 27/00; C12P 38/00
USPC .................................................. 435/65, 252.3
See application file for complete search history.

(56) References Cited

PUBLICATIONS

Bottini et al. Appl Microbiol Biotechnol (2004) 65: 497-503.*

\* cited by examiner

*Primary Examiner* — Tekchand Saidha
(74) *Attorney, Agent, or Firm* — McKee, Voorhees & Sease, PLC

(57) ABSTRACT

The present invention provides compositions and methods for modification of rhizobacteria to reduce or eliminate gibberellin production. The modified rhizobacteria are used in methods and compositions that alter the physiology of nodulating plants. These methods and compositions involve combining the modified rhizobacteria with a nodulating plant, or a seed or part thereof, or providing the modified rhizobacteria to a nodulating plant, or seed or part thereof. In another aspect, the invention involves the nodulating plants produced by these methods, wherein the nodulating plants have altered physiology as a result of association with the modified rhizobacteria.

10 Claims, 15 Drawing Sheets

3rd trifoliate wildtype:

3rd trifoliate gibberellin-deficient:

4th trifoliate wildtype:

4th trifoliate gibberellin-deficient:

5th trifoliate wildtype:

5th trifoliate gibberellin-deficient:

6th trifoliate wildtype:

6th trifoliate gibberellin-deficient:

MODIFICATION OF NITROGEN-FIXING RHIZOBACTERIA TO ENHANCE NODULATED PLANT RESISTANCE

CROSS REFERENCE TO RELATED APPLICATIONS

This application claims priority under 35 U.S.C. §119 to provisional application U.S. Ser. No. 61/996,674 filed May 14, 2014, herein incorporated by reference in its entirety.

GRANT REFERENCE

This invention was made with government support under Grant No. MCB0919735 awarded by National Science Foundation. The government has certain rights in the invention.

FIELD OF THE INVENTION

The invention relates generally to the fields of molecular biology, specifically relating to microbiology and botany. This invention also relates to the use of transgenic or mutant microbes, including rhizobacteria, to produce alterations in characteristics of nodulated plants, including increased resistance to plant pathogens.

BACKGROUND OF THE INVENTION

Bacteria play critical roles in biogeochemical cycles, such as the fixation of nitrogen. Although nitrogen makes up approximately 80% of the Earth's atmosphere, its bioavailability remains a major limitation, in particular to plant growth. This is due to the inability of plants to assimilate the diatomic nitrogen that occurs naturally in the atmosphere. Among plants, legumes uniquely host bacteria in nodules formed following invasion of their root cortical cells. These bacteria are typically from the Rhizobiales order of the Alphaproteobacteria, although others are from the Betaproteobacteria class, collectively these are referred to as rhizobia or rhizobacteria. Inside these nodules, the rhizobacteria develop into endosymbiont bacteroids, fixing nitrogen in exchange for carbon from their plant hosts. This agriculturally important collaboration is thought to be the main biological route for nitrogen fixation. For example, the relationship between soybean *Glycine max* and the associated nodulating rhizobacteria *Bradyrhizobium japonicum* is essential for the critical nitrogen-fixating properties that make this crop plant so agriculturally important. Of particular relevance here, a number of the rhizobacteria have been shown to produce plant growth hormones, such as the gibberellins, which are thought to further promote growth of the host plant.

Both legume and rhizobacterial species exhibit a surprising amount of specificity with respect to symbiotic partners. Only rarely can a given rhizobacterial species nodulate more than a few closely related plants. This specificity is due to bacterial and plant factors. The host plant secretes flavonoid inducers that elicit rhizobacterial production of lipochitooligosaccharide Nod factors, which are recognized by the host plant, with subsequent steps in the nodulation process being dependent on recognition of bacterial cell surface chemistry and effector proteins as well. However, the host plant also applies the usual defense mechanisms—e.g., microbe associated molecular pattern-triggered immunity and R-gene recognition of bacterial effectors—to restrict nodulation by unwanted strains. This complex signal exchange process exerts extreme evolutionary pressure on the rhizobacteria, which can be inferred, in part, from the presence of large plasmids or genomic islands with distinct G+C contents relative to the G+C content in the rest of the genome. These large plasmids or genomic islands contain the large set of genes required for nodulation, including nitrogen fixation. This presumably reflects the ability of horizontal transfer to spread these distinct genetic elements, enabling nodulation by the recipient rhizobacteria. Intriguingly, the prevalence of insertion sequences and phage integration is thought to promote rearrangement within these symbiotic nodules.

The nitrogen-fixing capacity imparted to soybean via nodulation of their roots by *B. japonicum* offers a clear advantage to the plant. Indeed, it is this nitrogen fixation that is largely responsible for the benefits of including soybean as a rotational crop. Such nodulation occurs as the product of highly specific partnerships formed between individual leguminous plant species and a particular species of rhizobacteria. This involves providing the rhizobacterial partner not only access to the interior of the host plant root, but also a hospitable environment, including feeding with photosynthetically fixed carbon. Intriguingly, presumably due to the dangers of establishing such an intimate relationship with a microbe, most legumes actually force their nodulating rhizobacterial partner to undergo a transition from the free-living form found in the soil to a terminally differentiated bacteriod form that essentially becomes a nitrogen-fixing organelle, and cannot go back to living in the soil. However, this is not true in soybean and other determinate nodule forming legumes, where the symbiotic microbe (e.g., *B. japonicum* for soybean) retains its usual form, and can go back to living in the soil.

The gibberellins are a large group of complex diterpenoid natural products, among which several have potent biological activity in plants, where they serve as hormones. Intriguingly, these phytohormones are made not only by the plants in which they serve to regulate growth and development, but by certain plant associated fungal and bacterial microbes as well. While gibberellin phytohormone biosynthesis has been largely elucidated for higher plants and fungi, which seem to have independently evolved/assembled the corresponding metabolic pathway, the basis for such biosynthesis in bacteria remains enigmatic. Even in higher plants, the origins of gibberellin metabolism remains obscure. Further, there have been recent discoveries demonstrating the existence of novel gibberellin metabolism (particularly catabolism) in higher plants, which have critical yet unexplored implications for flux in and the regulation of gibberellin metabolism.

Two terpene synthases have been characterized from a strain of *B. japonicum* (USDA110). These proved to be diterpene cyclases capable of successively converting the general diterpenoid precursor (E,E,E)-geranylgeranyl diphosphate (GGPP) into ent-copalyl diphosphate (ent-CPP) and, hence, to ent-kaurene, a precursor to the gibberellin phytohormones (FIG. 1). The relevant genes, blr2149 and blr2150, encode an ent-copalyl diphosphate synthase (CPS) and ent-kaurene synthase (KS), respectively. Notably, these two genes fall into a more extensive operon that was originally defined by Tully et al. (Appl. Environ. Microbiol. 1993, 59(12):4136) and suggested to be present in all rhizobia.

Gibberellins have played an important role in agriculture, as it was alterations in such phytohormone metabolism that led to high yielding semi-dwarf varieties of rice and wheat, which were a critical component of the "Green Revolution." The biosynthesis of gibberellin phytohormones by plant growth promoting bacteria that are commonly applied to legume crop plants offers additional significance. Further, the absolute requirement for gibberellin production in higher plants has provided a genetic reservoir of biosynthetic genes, duplication of which has led to a vast super-family (~7,000 known) of related diterpenoid natural products, exhibiting various biological activities and physiological roles (e.g., as defensive antibiotics). The production of gibberellins by *B. japonicum* has long been thought to promote plant growth as part of a symbiotic relationship. Although the genetic locus encoding the cellular machinery responsible for gibberellin production has previously been described, for example by Tully and Keister (Appl. Environ. Microbiol. 1993, 59(12):4136), the true role of bacterial gibberellin production has remained unclear.

Therefore, it is a primary object, feature, or advantage of the present invention to improve upon the state of the art.

It is a further object, feature, or advantage of the present invention to provide methods of altering the physiology of a plant, including enhancing pathogen resistance.

It is a further objective, feature or advantage of the present invention to provide methods for modifying rhizobacteria to eliminate or decrease bacterial gibberellin production.

It is a further objective, feature or advantage of the present invention to provide modified rhizobacteria that produce little or no gibberellin.

It is a further objective, feature or advantage of the present invention to provide methods of enhancing pathogen resistance in plants by reducing or eliminating gibberellin production by rhizobacteria in the nodules of the plants.

It is a further objective, feature or advantage of the present invention to provide rhizobacteria that have been modified to promote enhanced pathogen resistance in plants while still providing all the nitrogen-fixing benefits of nodulation.

It is a further objective, feature or advantage of the present invention to provide compositions comprising a nodulating plant and a modified rhizobacteria wherein the plant has altered physiology as a result of the modified rhizobacteria.

SUMMARY OF THE INVENTION

The present invention provides compositions and methods for modification of rhizobacteria to reduce or eliminate gibberellin production. In one embodiment, rhizobacteria are modified to decrease or eliminate the activity or expression of one or more proteins encoded by the gibberellin locus of the rhizobacteria. In another aspect, rhizobacteria with little or no gibberellin production may be used in methods and compositions that alter the physiology of nodulating plants. In some aspects, the modified physiology may include for example, increased plant height, increased plant biomass, increased plant yield and the like. These methods and compositions involve combining rhizobacteria that are mutated or modified to decrease or eliminate gibberellin production with a nodulating plant, or a seed or part thereof, or providing the rhizobacteria to a nodulating plant, or seed or part thereof. In another aspect, the invention involves the nodulating plants produced by these methods, wherein the nodulating plants have altered physiology as a result of association with the modified rhizobacteria.

In an aspect of the invention, the production of gibberellin by rhizobacteria has allowed the identification of relevant genes to obtain a gene knock-out strain that no longer is capable of making gibberellins. In an aspect, the mutant is employed in nodulated plants, such as leguminous crops, including soybeans. Strikingly, this mutant is not impaired in its ability to nodulate and provide nitrogen to soybean, or promote plant growth. Instead, the resulting nodules are smaller and many of the enclosed bacteroids have lost their viability to go back to a free-living state in the soil, suggesting that the mutant has become much less resistant to the ability of soybean to promote differentiation of *B. japonicum* into bacteriods (which can no longer go back to free-living bacteria in the soil). Accordingly, it appears that *B. japonicum* produces gibberellins to both increase nodule size and suppress this defensive response rather than promote soybean plant growth. The inventors have modified *B. japonicum* such that it can no longer produce gibberellins, which leads to more disease resistant soybean plants, while still providing all the nitrogen-fixing benefits of nodulation. The gibberellin operon has also been identified in other rhizobacteria, indicating that the beneficial effects of removing or inhibiting the gibberellin production is more broadly applicable to any of these nodulating, nitrogen-fixing bacteria in symbiosis with various species of legumes or other nodulating plants. In addition, other physiological improvements may be observed. The compositions and methods for improving plant pathogen resistance by providing modified rhizobacteria impart an obvious agricultural benefit.

In one aspect of the invention, the conservation of the CPS and KS from this operon and the production of the upstream GGPP by the isoprenyl diphosphate synthase encoded by the adjacent gene in the operon is demonstrated. In a further aspect, the operon exhibits a scattered distribution within the rhizobacteria. While examples are found in all four major genera from the Rhizobiales, with conservation of the ability to produce ent-kaurene, as well as uncharacterized examples from the Betaproteobacteria, the uneven distribution of the operon suggests that such diterpenoid production provides a selective advantage only under certain conditions.

In one embodiment, the present invention provides methods for altering the physiology of nodulating plants. In one aspect, the alteration is accomplished by providing rhizobacteria that have been modified to produce little or no gibberellin and permitting nodulation of the plants by the modified rhizobacteria.

In another embodiment, the present invention provides methods for enhancing pathogen resistance in nodulating plants by providing rhizobacteria that have been modified to produce little or no gibberellin.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1A:
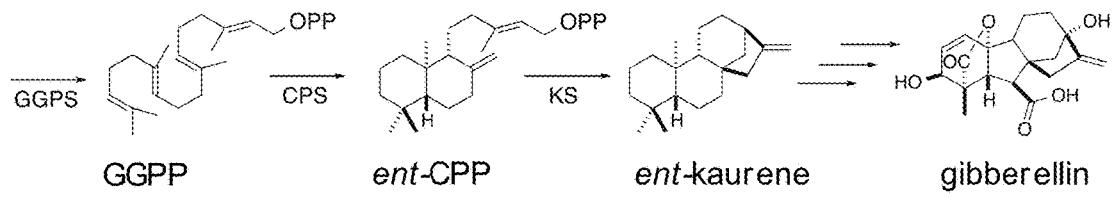
FIG. 1 (A-B) shows gibberellin biosynthesis pathway and operon identified in *B. japonicum*. (A) The known enzymatic components of the gibberellin biosynthetic pathway are shown, along with the intermediate compounds. (B) Relative location of the genes (large arrows) in the gibberellin biosynthetic operon of *B. japonicum*. Gene names are shown within each arrow.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Similarly, recitation of "up to" a value includes all values between zero and the recited value, and recitation of "at least" a value includes all values greater than the recited value.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e. g., Diagnostic Molecular Microbiology: Principles and Applications, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W. H. Freeman and Company.

By "encoding" or "encoded", with respect to a specified nucleic acid, is meant comprising the information for translation into the specified protein. A nucleic acid encoding a protein may comprise intervening sequences (e. g., introns) within translated regions of the nucleic acid, or may lack such intervening non-translated sequences (e. g., as in cDNA). The information by which a protein is encoded is specified by the use of codons. Typically, the amino acid sequence is encoded by the nucleic acid using the "universal" genetic code. However, variants of the universal code, such as are present in some plants, algae, animal, and fungal mitochondria, the bacterium *Mycoplasma* capricolum, or the ciliate Macronucleus, may be used when the nucleic acid is expressed therein. When the nucleic acid is prepared or altered synthetically, advantage can be taken of known codon preferences of the intended host where the nucleic acid is to be expressed.

As used herein "full-length sequence" in reference to a specified polynucleotide or its encoded protein means having the entire amino acid sequence of a native (nonsynthetic), endogenous, biologically active form of the specified protein. Methods to determine whether a sequence is full-length are well known in the art including such exemplary techniques as northern or western blots, primer extension, S 1 protection, and ribonuclease protection. See, e. g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN <u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

The terms "genetically modified" and "genetic modification" as used herein refer to alteration of a polynucleotide or gene that renders a protein, peptide, polynucleotide, gene, or other molecule non-naturally occurring. Genetic modification includes knockdown and knockout of a target gene, locus, or operon, as well as insertions, deletions, inversions and the like. Modifications may be produced by methods known in the art, for example by use of gene editing effectors including Zinc Finger Nucleases (ZFNs), Transcription Activator-Like Effector Nucleases (TALENs), the Clustered Regularly Interspaced Short Palindromic Repeats/ CAS9 (CRISPR/Cas9) system, and meganuclease re-engineered as homing endonucleases. The terms also include the use of transgenic procedures and techniques, including, for example, where the change is relatively small and/or does not introduce DNA from a foreign species. The terms include gene editing techniques, as well as and/or in addition to other techniques and processes that alter or modify the nucleotide sequence of a gene or genes, or modify or alter the expression of a gene or genes.

As used herein, the term "gibberellin" refers to hormones that act in plants, which are tetracyclic diterpenoid acids that are synthesized by the terpenoid pathway. Gibberellins derived via the ent-gibberellane skeleton, but are synthesised via ent-kaurene intermediate. Gibberellins may be either 19 carbon forms or 20 carbon forms. The 19-carbon gibberellins, such as gibberellic acid, have lost carbon 20 and, in place, possess a five-member lactone bridge that links carbons 4 and 10. Gibberellins are understood to also include hydroxylated or multiply-hydroxylated forms, for example tetracyclic diterpene acids that possess hydroxyl groups on both carbon 3 and carbon 13. The term gibberellin also includes analogues of naturally occurring gibberellin compounds that retain biological activity. The basic structure of gibberellin is provided below:

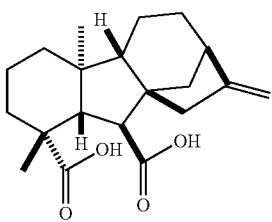 [SMILES: C=C1C[C@]23C[C@H]1CC[C@H]2[C@]1(C)CCC[C@@](C)(C(=O)O)[C@H]1[C@@H]3C(=O)O]

An example of a gibberellin (Gibberellin A9; GA9) is shown below:

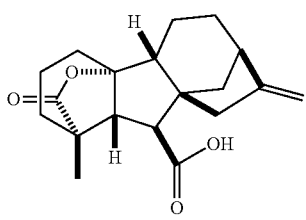 [SMILES: C=C1C[C@]23C[C@H]1CC[C@H]2[C@@]12CCC[C@@](C)(C(=O)O1)[C@H]2[C@@H]3C(=O)O]

An example of a methylated gibberellin (Gibberellin A9 methyl ester, MeGA9) is shown below:

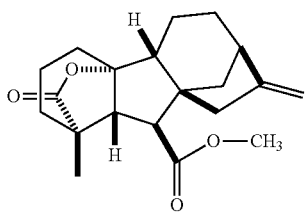 [SMILES: C=C1C[C@]23C[C@H]1CC[C@H]2[C@@]12CCC[C@@](C)(C(=O)O1)[C@H]2[C@@H]3C(=O)OC]

Other gibberellin molecules, including methylated gibberellins and other modifications, are known to persons of skill in the art. A "gibberellin locus" or "gibberellin operon" refers to a region of a genome or chromosome that contains one or more genes encoding products that play a role in the synthesis or production of gibberellin or an intermediate of gibberellin production, or a homologue thereof. The locus or operon may be characterized by homology to a known gibberellin locus or operon, for example the B. japonicum gibberellin biosynthetic operon.

The term "gibberellin-deficient" as used herein is understood to describe organisms for which gibberellin production is reduced or eliminated, compared to organisms of the same species, type, strain, or the like. Such gibberellin-deficient organisms may be the result of modification or mutation, including naturally occurring and non-naturally occurring mutations or modifications.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be rhizobacteria or other prokaryotic cells such as E. coli, or eukaryotic cells such as yeast, insect, amphibian, or mammalian cells.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nodulating plant" means a plant that forms root nodules due to association with symbiotic nitrogen-fixing bacteria. Nodulating plants are primarily of the Fabaceae or Leguminosae family, including, for example, *Glycine max* (soybean), *Phaseolus* (beans), *Pisum sativum* (pea), *Cicer arietinum* (chickpeas), *Medicago sativa* (alfalfa), *Arachis hypogaea* (peanut), *Ceratonia siliqua* (carob), and *Glycyrrhiza glabra* (liquorice). Other nodulating plants include non-legume genera like *Parasponia* and *Alnus*. Root nodules formed by nodulating plants due to association with symbiotic nitrogen-fixing bacteria may be determinate nodules or indeterminate nodules.

The term "nodulation" refers to the association between nodulating plants and rhizobacteria that inhabit the root nodules of the plant. In general, the term encompasses the following process: Nodulating plants release compounds called flavonoids from their roots, which trigger the production of nod factors by the bacteria. When the nod factor is sensed by the root, a number of biochemical and morphological changes happen: cell division is triggered in the root to create the nodule, and the root hair growth is redirected to wind around the bacteria multiple times until it fully encapsulates 1 or more bacteria. The bacteria encapsulated divide multiple times, forming a microcolony. From this microcolony, the bacteria enter the developing nodule through a structure called an infection thread, which grows through the root hair into the basal part of the epidermis cell, and onwards into the root cortex; they are then surrounded by a plant-derived membrane and differentiate into bacteroids that fix nitrogen. The term "association" as used with respect to nodulating plants and rhizobacteria encompasses nodulation, and any and all steps in the process.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning-A Laboratory Manual, 2nd ed., Vol. 1-3 (1989); and Current Protocols in Molecular Biology, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

The term "plant pathogen" means a compound or composition or living material, such as a microorganism, including viruses, bacteria, and fungi, which cause disease or damage to the plant.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid (s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitization, and they may be circular, with or without branching, generally as a result of post translation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. An "inducible" or "repressible" promoter is a promoter which is under environmental control. Examples of environmental conditions that may affect transcription by inducible promoters include presence within a root nodule, or existing free in the soil. Tissue specific, tissue preferred, cell type specific, and inducible promoters constitute the class of "non-constitutive" promoters. Examples of inducible promoters include Lac promoter, Trp promoter, tetA promoter and cadA promoter. A "constitutive" promoter is a promoter which is active under most environmental conditions. Examples of constitutive promoters include Ubiquitin promoter, actin promoter, OXP20 promoter, heat shock protein (hsp) promoter variants, and the like.

A skilled person appreciates a promoter sequence can be modified to provide for a range of expression levels of an operably linked heterologous nucleic acid molecule. Less than the entire promoter region can be utilized and the ability to drive expression retained. However, it is recognized that expression levels of mRNA can be decreased with deletions of portions of the promoter sequence. Thus, the promoter can be modified to be a weak or strong promoter. A promoter is classified as strong or weak according to its affinity for RNA polymerase (and/or sigma factor); this is related to how closely the promoter sequence resembles the ideal consensus sequence for the polymerase. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

As used herein "recombinant" includes reference to a cell or vector that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" is used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "rhizobacteria" refers to root-colonizing bacteria that form symbiotic relationships with plants, and in particular nodulating plants. The term "rhizobacteria" includes bacteria commonly referred to as "rhizobia." Rhizobacteria may be parasitic or symbiotic/mutualistic. The term "rhizobacteria" is synonymous with and used interchangeably with "plant growth-promoting rhizobacteria" (PGPRs) and "nodulating bacteria". Rhizobacteria may be rhizospheric or endophytic. Rhizospheric PGPRs colonize the surface of the root, or superficial intercellular spaces of the host plant, often forming root nodules. Endophytic PGPRs reside and grow within the host plant in the apoplastic space. Rhizobacteria may interact with nodulating plants through different direct and indirect mechanisms, including increased mineral nutrient solubilization and nitrogen fixation, thereby making nutrients available for the plant; repression of soilborne pathogens, for example by the production of hydrogen cyanide, siderophores, antibiotics, and/or competition for nutrients; improving plant stress tolerance to drought, salinity, and metal toxicity; and/or production of phytohormones. Rhizobacteria include, for example, bacteria in the geni *Azospirillum* (e.g., *Azospirillum fluorescens*, *Azospirillum lipoferum*), *Acetobacter diazotrophicus*, *Herbaspirillum seropedicae*, *Azoarcus* spp. and *Azotobacter*, and also includes, for example, *Bosea* (e.g., *B. lathyri*, *B. lupine*, *B. robiniae*); *Bradyrhizobium* (e.g., *B. arachidis*, *B. canariense*, *B. cytisi*, *B. daqingense*, *B. denitrificans*, *B. diazoefficiens*, *B. elkanii*, *B. huanghuaihaiense*, *B. iriomotense*, *B. japonicum*, *B. jicamae*, *B. lablabi*, *B. liaoningense*, *B. pachyrhizi*, *B. rifense*, *B. yuanmingense*); *Ochrobactrum* (e.g., *O. cytisi*, *O. lupine*); *Azorhizobium* (e.g., *A. caulinodans*, *A. doebereinerae*); *Devosia* (e.g., *D. neptuniae*); *Methylobacterium* (e.g., *M. nodulans*); *Microvirga* (e.g., *M. lotononidis*, *M. lupine*, *M. zambiensis*); *Aminobacter* (e.g., *Aminobacter anthyllidis*); *Mesorhizobium* (e.g., *M. abyssinicae*, *M. albiziae*, *M. alhagi*, *M. amorphae*, *M. australicum*, *M. camelthorni*, *M. caraganae*, *M. chacoense*, *M. cicero*, *M. gobiense*, *M. hawassense*, *M. huakuii*, *M. loti*, *M. mediterraneum*, *M. metallidurans*, *M. muleiense*, *M. opportunistum*, *M. plurifarium*, *M. qingshengii*, *M. robiniae*, *M. sangaii*, *M. septentrionale*, *M. shangrilense*, *M. shonense*, *M. tamadayense*, *M. tarimense*, *M. temperatum*, *M. tianshanense*); *Phyllobacterium* (e.g., *P. ifriqiyense*, *P. leguminum*, *P. trifolii*); *Rhizobium* (e.g., *R. alamii*, *R. alkalisoli*, *R. cauense*, *R. cellulosilyticum*, *R. daejeonense*, *R. etli*, *R. fabae*, *R. galegae*, *R. gallicum*, *R. giardinii*, *R. grahamii*, *R. hainanense*, *R. halophytocola*, *R. helanshanense*, *R. herbae*, *R. huautlense*, *R. indigoferae*, *R. leguminosarum*, *R. leucaenae*, *R. loessense*, *R. lupine*, *R. lusitanum*, *R. mesoamericanum*, *R. mesosinicum*, *R. miluonense*, *R. mongolense*, *R. multihospitium*, *R. nepotum*, *R. oryzae*, *R. petrolearium*, *R. phaseoli*, *R. pisi*, *R. pusense*, *R. qilianshanense*, *R. sphaerophysae*, *R. sullae*, *R. taibaishanense*, *R. tibeticum*, *R. tropici*, *R. tubonense*, *R. undicola*, *R. vallis*, *R. vignae*, *R. yanglingense*); *Shinella* (e.g., *S. kummerowiae*); *Sinorhizobium/Ensifer* (e.g., *S. abri*, *E. adhaerens*, *S. americanum*, *S. arboris*, *S. chiapanecum*, *S. fredii*, *E. garamanticus*, *S. indiaense*, *S. kostiense*, *S. kummerowiae*, *S. medicae*, *S. meliloti*, *E. mexicanus*, *E. numidicus*, *E. psoraleae*, *S. saheli*, *E. sesbaniae*, *E. sojae*, *S. terangae*); *Burkholderia* (e.g., *B. caribensis*, *B. dolosa*, *B. mimosarum*, *B. nodosa*, *B. phymatum*, *B. sabiae*, *B. tuberum*); *Cupriavidus* (e.g., *C. taiwanensis*); *Pseudomonas putida*; and *Allorhizobium*.

The term "selectively hybridizes" includes reference to hybridization, under stringent hybridization conditions, of a nucleic acid sequence as to other biologics. Thus, under designated immunoassay conditions, the specified antibodies bind to an analyte having the recognized epitope to a substantially greater degree (e. g., at least 2-fold over background) than to substantially all analytes lacking the epitope which are present in the sample. Specific binding to an antibody under such conditions may require an antibody that is selected for its specificity for a particular protein. For example, antibodies raised to the polypeptides of the present invention can be selected from to obtain antibodies specifically reactive with polypeptides of the present invention.

The proteins used as immunogens can be in native conformation or denatured so as to provide a linear epitope.

The term "stringent conditions" or "stringent hybridization conditions" includes reference to conditions under which a probe will hybridize to its target sequence, to a detectably greater degree than to other sequences (e. g., at least 2-fold over background). Stringent conditions are sequence-dependent and will be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30 C for short probes (e. g., 10 to 50 nucleotides) and at least about 60 C for long probes (e. g., greater than 50 nucleotides). Stringent conditions may also be achieved with the addition of destabilizing agents such as formamide. Exemplary low stringency conditions include hybridization with a buffer solution of 30 to 35%0 formamide, 1 MNaCI, 1% SDS (sodium dodecyl sulphate) at 37 C, and a wash in 1× to 2×SSC (20×SSC=3.0 MNaCI/0.3 M trisodium citrate) at 50 to 55 C. Exemplary moderate stringency conditions include hybridization in 40 to 45% formamide, 1 MNaCI, 1% SDS at 37 C, and a wash in <RTI 0.5× to 1×SSC at 55 to 60 C. Exemplary high stringency conditions include hybridization in 50% formamide, 1 MNaCI, 1% SDS at 37 C, and a wash in 0.1×SSC at 60 to 65 C. Specificity is typically the function of post-hybridization washes, the critical factors being the ionic strength and temperature of the final wash solution. For DNA/DNA hybrids, the Tm can be approximated from the equation of Meinkoth and Wahl, Anal. Biochem., 138: 267-284 (1984):Tm=81.5 C+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1 C for each 1% of mismatching; thus, Tm, hybridization and/or wash conditions can be adjusted to hybridize to sequences of the desired identity. For example, if sequences with >90% identity are sought, the Tm can be decreased 10 C. Generally, stringent conditions are selected to be about 5 C lower than the thermal melting point (Tm) for the specific sequence and its complement at a defined ionic strength and pH. However, severely stringent conditions can utilize a hybridization and/or wash at 1, 2, 3, or 4 C lower than the thermal melting point (Tm); moderately stringent conditions can utilize a hybridization and/or wash at 6, 7, 8, 9, or 10 C lower than the thermal melting point (Tm); low stringency conditions can utilize a hybridization and/or wash at 11, 12, 13, 14, 15, or 20 C lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45 C (aqueous solution) or 32 C (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic" includes reference to a plant or bacteria which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein. The following terms are used to describe the sequence relationships between a polynucleotide/polypeptide of the present invention with a reference polynucleotide/polypeptide: (a)"reference sequence", (b)"comparison window", (c) "sequence identity", and (d)"percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the . . . in the GCG Wisconsin Genetics Software Package, Version 10 (available from Accelrys Inc., 9685 Scranton Road, San Diego, Calif., USA). The CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215: 403-410 (1990); and, Altschul et al., Nucleic Acids Res. 25: 3389-3402 (1997).

Software for performing BLAST analyses is publicly available (e.g., through the National Center for Biotechnology Information www at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). One measure of similarity provided by the BLAST algorithm is the smallest sum probability (P(N)), which provides an indication of the probability by which a match between two nucleotide or amino acid sequences would occur by chance. BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

Unless otherwise stated, nucleotide and protein identity/similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (J. Mol. Biol. 48: 443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89: 10915).

Multiple alignment of the sequences can be performed using the CLUSTAL method of alignment (Higgins and Sharp (1989) CABIOS. 5: 151-153) with the default parameters (GAPPENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e. g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e. g., according to the algorithm of Meyers and Miller, Computer Applic. Biol. Sci., 4: 11-17 (1988) e. <RTI g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Sequence, and Strain, and Deposit Information

The full chromosomal genomic sequence of *B. japonicum* is available through the PubMed Genome database and GenBank. The NCBI Reference Sequence is NC_017249.1 and the GenBank ID is AP012206.1.

*Bradyrhizobium japonicum* exhibits heterogeneities among rhizobacteria assigned to this species. Strains assigned to *B. japonicum* group Ia, including USDA 110, have been proposed to be different enough from the *B. japonicum* type strain USDA 6(T) and closely related strains, with attendant morphophysiological, genotypic and genomic evidence, to support their reclassification into a novel species, for which the name *Bradyrhizobium diazoefficiens* sp. nov. has been proposed. The genome of USDA 110 (*B. diazoefficiens*) is available through PubMed Genome database. The NCBI Reference Sequence is NC_004463.1. USDA 110 (*B. diazoefficiens*) is available through the *Rhizobium* Culture Collection, U.S. Department of Agriculture Agricultural Research Service, Beltsville, Md.

The gibberellin operon of *B. japonicum* has been previously described by Raymond E. Tully et al. *Identification and sequencing of a cytochrome P450 gene cluster from Bradyrhizobium japonicum* 1998 (243-255). The sequence of the locus is available through the Genbank database. The GenBank ID is U12678.1.

Modified Rhizobacteria

The present invention involves rhizobacteria that have been modified to reduce or eliminate gibberellin production. The modified rhizobacteria are useful for producing alterations in the physiology of plant with which they become associated, i.e. through nodulation of the roots of the plant. According to one aspect of the invention, the modified, gibberellin-deficient rhizobacteria may be any rhizobacteria. In a preferred embodiment, the rhizobacteria is *B. japonicum*.

Modification of the Gibberellin Locus in Rhizobacteria

In one aspect, the invention involves using rhizobacteria with reduced or deficient gibberellin production. The reduced or deficient gibberellin production may, for example, be due to naturally occurring mutation of the bacteria, or may be by intentional action to reduce or eliminate gibberellin production, such as by modification of the bacteria.

In another aspect, the invention involves rhizobacteria that are modified to decrease or eliminate the production of gibberellin, gibberellin precursors or intermediates, or homologues thereof.

In a preferred embodiment, modification of rhizobacteria involves alteration of one or more bacterial genes within the gibberellin locus or operon of said rhizobacteria, or a locus or operon homologous to the gibberellin operon of *B. japonicum*. In one embodiment, modification of rhizobacteria involves targeted interruption of one or more genes within the gibberellin locus of the bacteria. In another preferred embodiment, modification involves excising or replacing one or more of these genes, up to the entire gibberellin locus of the bacteria.

Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event.

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant/algae species. Once a phylogenic tree for a gene family of one species has been constructed using a program such as CLUSTAL (Thompson et al. (1994) Nucleic Acids Res. 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

Modification of rhizobacteria may be carried out by any of the methods, techniques, or processes commonly known in the art that alter or modify the nucleotide sequence of a gene or genes, or modify or alter the expression of a gene or genes including, for example, knockout, knockdown, insertion, deletion, inversion and the like. Such methods include, for example, use of gene editing effectors including Zinc Finger Nucleases (ZFNs), Transcription Activator-Like Effector Nucleases (TALENs), the Clustered Regularly Interspaced Short Palindromic Repeats/CAS9 (CRISPR/Cas9) system, and meganuclease re-engineered as homing endonucleases. Modifications may also include the use of transgenic procedures and techniques, including, for example, where the change is relatively small and/or does not introduce DNA from a foreign species.

According to one aspect of the invention, the nucleotide sequence of one or more genes within a gibberellin locus may be modified by mutagenesis. Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector, which exists in both a single stranded and double stranded form. Typical vectors useful in site-directed mutagenesis include vectors such as the M13 phage. These phages are readily commercially available and their use is generally well known to those skilled in the art. Double stranded plasmids also are routinely employed in site directed mutagenesis, which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

In some embodiments, methods may be utilized to reduce or eliminate the activity of the gibberellin biosynthetic pathway in a rhizobacteria, such as by reducing or eliminating one or more proteins encoded by the gibberellin locus of the rhizobacteria. This may be accomplished, for example, by transforming the rhizobacteria with an expression cassette that expresses a polynucleotide that inhibits the expression of one or more proteins encoded by the gibberellin locus of the rhizobacteria. The polynucleotide may inhibit the expression of one or more proteins encoded by the gibberellin locus of the rhizobacteria directly, by preventing transcription or translation of messenger RNA for one or more proteins encoded by the gibberellin locus of the rhizobacteria, or indirectly, by encoding a polypeptide that inhibits the transcription or translation of one or more genes in the gibberellin locus of the rhizobacteria. Methods for inhibiting or eliminating the expression of a gene in a bacteria are well known in the art, and any such method may be used in the present invention to inhibit the expression of one or more proteins encoded by the gibberellin locus of the rhizobacteria.

In accordance with the present invention, the expression of one or more proteins encoded by the gibberellin locus of the rhizobacteria is inhibited if the protein level of the one or more proteins encoded by the gibberellin locus of the rhizobacteria is less than 70% of the protein level of the same one or more proteins encoded by the gibberellin locus of the rhizobacteria in a rhizobacteria that has not been genetically modified or mutagenized to inhibit the expression of that one or more proteins encoded by the gibberellin locus of the rhizobacteria. In particular embodiments of the invention, the protein level of the one or more proteins encoded by the gibberellin locus of the rhizobacteria in a modified rhizobacteria according to the invention is less than 60%, less than 50%, less than 40%, less than 30%, less than 20%, less than 10%, less than 5%, or less than 2% of the protein level of the same one or more proteins encoded by the gibberellin locus of the rhizobacteria in a rhizobacteria that is not a mutant or that has not been genetically modified to inhibit the expression of one or more proteins encoded by the gibberellin locus of the rhizobacteria. The expression level of the one or more proteins encoded by the gibberellin locus of the rhizobacteria may be measured directly, for example, by assaying for the level of one or more proteins encoded by the gibberellin locus of the rhizobacteria expressed in the rhizobacteria, or indirectly, for example, by measuring the phenotypic changes in the rhizobacteria. Methods for performing such assays are described elsewhere herein.

In other embodiments of the invention, the activity of the one or more proteins encoded by the gibberellin locus of the rhizobacteria is reduced or eliminated by transforming a bacterial cell with an expression cassette comprising a polynucleotide encoding a polypeptide that inhibits the activity of one or more proteins encoded by the gibberellin locus of the rhizobacteria. The activity of one or more proteins encoded by the gibberellin locus of the rhizobacteria is inhibited according to the present invention if the activity of the one or more proteins encoded by the gibberellin locus of the rhizobacteria is less than 70% of the activity of the same one or more proteins encoded by the gibberellin locus of the rhizobacteria in a rhizobacteria that has not been modified to inhibit the activity of one or more proteins encoded by the gibberellin locus of the rhizobacteria. In particular embodiments of the invention, the activity of one or more proteins encoded by the gibberellin locus of the rhizobacteria in a modified rhizobacteria according to the invention is less than 60%, less than 50%, less than 40%, less than 30%, less than 20%, less than 10%, or less than 5% of the activity of the same gibberellin biosynthetic pathway in a rhizobacteria that has not been modified to inhibit the expression of one or more proteins encoded by the gibberellin locus of the rhizobacteria. The activity of one or more proteins encoded by the gibberellin locus of the rhizobacteria is "eliminated" according to the invention when it is not detectable by the assay methods described elsewhere herein. Methods of determining the alteration of activity of one or more proteins encoded by the gibberellin locus of the rhizobacteria are described elsewhere herein.

Thus, many methods may be used to reduce or eliminate the activity of one or more proteins encoded by the gibberellin locus of the rhizobacteria.

Alteration of Nodulating Plant Physiology

In one aspect, the present invention involves altering the physiology of nodulating plants. The changes in plant physiology are produced by providing to the nodulating plant one or more rhizobacteria that have reduced or absent gibberellin production. The rhizobacteria may be genetically modified, or may be naturally occurring gibberellin-deficient strains or mutants.

In one aspect of the invention, rhizobacteria with reduced or eliminated gibberellin production are provided to a nodulating plant. The particular type of nodulating plant may be dictated by the type of rhizobacteria. For example, in a preferred embodiment, the modified rhozobacterium is *B. japonicum*, and the nodulating plant is *Glycine max* (soybean). Providing the modified rhizobacterium to the plant results in alterations in the plant's physiology, compared to a plant that is associated with an unmodified or wild-type rhizobacterium of the same species, strain, or type.

Physiological Changes in Nodulating Plants Induced by Modified Rhizobacteria

In one embodiment, the present invention involves providing the modified rhizobacteria to nodulating plants which induces a change in the physiology or characteristic of the plant compared to the same plant provided with a non-modified rhizobacteria. Physiological or characteristic changes may include, for example, increased plant height, increased plant biomass, increased plant yield, such as increased number, size, or total mass of fruit, seeds, or other products. In a preferred embodiment, the physiological change in the plant is increased resistance to diseases and/or pathogens.

The present invention can provide a method for producing a plant exhibiting increased individual plant weight, increased weight of a given tissue per individual plant, improved productivity of a given substance per individual plant, or increased content of a given substance in a given tissue of a plant. Changes in a characteristic can be an increase that may also represent a decrease; for example an increase in disease resistance may also represent a decrease in susceptibility. An increase in a characteristic can be expressed as a percentage or fold increase in comparison to the same plant provided with a non-modified rhizobacteria. For example, a characteristic may be increased by at least 1%, at least 5%, at least 10%, at least 25%, at least 50%, at least 100%, at least 200%, at least, 300%, at least 400%, or at least 500%. Alternatively, a characteristic may be decreased by at least 1%, at least 5%, at least 10%, at least 25%, at least 50%, at least 100%, at least 200%, at least, 300%, at least 400%, or at least 500%.

In one exemplary embodiment, plants provided with modified rhizobacteria have increased plant height compared to plants provided with non-modified rhizobacteria. In a further aspect, the increase is between about 1% and about 100%, between about 5% and about 50%, or about 10%. In another exemplary embodiment, plants provided with modified rhizobacteria have decreased disease susceptibility compared to plants provided with non-modified rhizobacteria. In a further aspect, decreased disease susceptibility may be demonstrated by, for example, decreased leaf discoloration. The decrease can be, for example, between about 1% and about 100%, between about 5% and about 95%, between about 10% and about 90%, or between about 25% and about 75%.

The modified rhizobacteria may be provided to the plant in any manner that permits the rhizobacteria and the plant to interact sufficiently to allow physiological changes in the plant. For example, the modified rhizobacteria may be inoculated onto plants or the roots of plants, directly applied to seeds of the plant prior to planting, or the modified rhizobacteria may be present in or added to the soil or other medium in which the plant is grown.

Resistance to Plant Pathogens

In one aspect, the invention comprises modifying the ability of nodulating plants to resist pathogens and diseases by providing the modified rhizobacteria described herein to the plants. Providing the modified rhizobacteria may increase the resistance of the plant to one or more pathogens or diseases. An increased resistance may comprise a decrease or absence of disease symptoms or damage, or decrease or absence of infection by a pathogen. Examples of diseases to which resistance may be increased include, for example, soybean cyst nematode, brown stem rot, *Phytophthora* root rot, soybean mosaic virus, and sudden death syndrome (SDS). Plant pathogens may be bacteria, viruses, fungi, or invertebrate pathogens (i.e. nematodes). These pathogens may be from a variety of genera including, for example, *Alternaria, Ascochyta, Aspergillus, Botrytis, Cer-* cospora, Colletotrichum, Diplodia, Erwinia, Erysiphe, Fusarium, Gaeumanomyces, Helminthosporium, Macrophomina, Magnaporthe, Mycosphaerella, Nectria, Peronospora, Phoma, Phymatotrichum, Phytophthora, Plasmopara, Podosphaera, Pseudomonas, Puccinia, Puthium, Pyrenophora, Pyricularia, Pythium, Rhizoctonia, Scerotium, Sclerotinia, Septoria, Thielaviopsis, Uncinula, Venturia, and Verticillium, and Xanthomonas.

Bacterial plant pathogens may include, for example, *Agrobacterium tumefaciens, Clavibacter michiganensis, Erwinia carotovora* pv. *carotovora, Xanthomonas campestris Pammel* pv. *Phaseoli, Ralstonia solanacearum, Bacillus subtilis (Bacillus* seed decay), *Pseudomonas savastonoi* pv. *glycinea* (Bacterial blight), *Pseudomonas syringae* subsp. *syringae* (Bacterial crinkle-leaf), *Xanthomonas axonopodis* pv. *glycines*, (Bacterial pustule), *Curtobacterium flaccumfaciens* pv. *flaccumfaciens*, (Bacterial tan spot), *Curtobacterium flaccumfaciens* pv. *flaccumfaciens, Ralstonia solanacearum*, (Bacterial wilt), and *Pseudomonas syringae* pv. *tabaci* (Wildfire)

Fungal plant pathogens may include, for example, *Phakopsora pachyrhizi, Phakopsora meibomiae* (Asian Soybean Rust), *Colletotrichum truncatum, Colletotrichum dematium* var. *truncatum, Glomerella glycines* (Soybean Anthracnose), *Phytophthora sojae* (*Phytophthora* root and stem rot), *Sclerotinia sclerotiorum* (*Sclerotinia* stem rot), *Fusarium solani* f. sp. *glycines* (sudden death syndrome), *Fusarium* spp. (*Fusarium* root rot), *Macrophomina phaseolina* (charcoal rot), *Septoria glycines*, (Brown Spot), *Pythium aphanidermatum, Pythium debaryanum, Pythium irregulare, Pythium ultimum, Pythium myriotylum, Pythium torulosum* (*Pythium* seed decay), *Diaporthe phaseolorum* var. *sojae* (Pod blight), *Phomopsis longicola* (Stem blight), *Phomopsis* spp. (*Phomopsis* seed decay), *Peronospora manshurica* (Downy Mildew), *Rhizoctonia solani* (*Rhizoctonia* root and stem rot, *Rhizoctonia* aerial blight), *Phialophora gregata* (Brown Stem Rot), *Diaporthe phaseolorum* var. *caulivora* (Stem Canker), *Cercospora kikuchii* (Purple Seed Stain), *Alternaria* sp. (Target Spot), *Cercospora sojina* (Frogeye Leafspot), *Sclerotium rolfsii* (Southern blight), *Arkoola nigra* (Black leaf blight), *Thielaviopsis basicola*, (Black root rot), *Choanephora infundibulifera, Choanephora trispora* (*Choanephora* leaf blight), *Leptosphaerulina trifolii* (*Leptosphaerulina* leaf spot), *Mycoleptodiscus terrestris* (*Mycoleptodiscus* root rot), *Neocosmospora vasinfecta* (*Neocosmospora* stem rot), *Phyllosticta sojicola* (*Phyllosticta* leaf spot), *Pyrenochaeta glycines* (*Pyrenochaeta* leaf spot), *Cylindrocladium crotalariae* (Red crown rot), *Dactuliochaeta glycines* (Red leaf blotch), Spaceloma *glycines* (Scab), *Stemphylium botryosum* (*Stemphylium* leaf blight), *Corynespora cassiicola* (Target spot), *Nematospora coryli* (Yeast spot), and *Phymatotrichum omnivorum* (Cotton Root Rot).

Viral plant pathogens may include, for example, Alfamovirus (Alfafa mosaic virus, AMV), Comovirus (bean pod mottle virus, BPMV), Potyvirus (bean yellow mosaic virus, BYMV), Bromovirus (cowpea chlorotic mottle virus, CCMV), Begomovirus (mung bean yellow mosaivc virus, MYMV), Potyvirus (peanut mottle virus, PeMoV), Potyvirus (peanut stripe virus, PStV), Cucumovirus (peanut stunt virus, PSV), Caulimovirus (soybean chlorotic mottle virus, SbCMV), Begomovirus (soybean crinkle leaf virus, SCLV), Luteovirus (soybean dwarf virus, SbDV), Potyvirus (soybean mosaic virus, SMV), Nepovirus (soybean severe stunt virus, SSSV), and Nepovirus (tobacco ringspot virus, TRSV).

Invertebrate or nematode plant pathogens may include, for example, *Aphis glycines* (Soybean aphid), *Heterodera glycines* (Soybean cyst nematode), *Meloidogyne arenaria, Meloidogyne hapla, Meloidogyne incognita, Meloidogyne javanica* (Root knot nematode), *Hoplolaimus Columbus, Hoplolaimus galeatus, Hoplolaimus magnistylus* (Lance nematode), *Pratylenchus* spp. (Lesion nematode), *Paratylenchus projectus, Paratylenchus tenuicaudatus* (Pin nematode), *Rotylenchulus reniformis* (Reniform nematode), *Criconemella ornata* (Ring nematode), *Hemicycliophora* spp. (Sheath nematode), *Heliocotylenchus* spp. (Spiral nematode), *Belonolainus gracilis, Belonolainus longicaudatus* (Sting nematode), *Quinisulcius acutus, Tylenchorhynchus* spp. (Stunt nematode), and *Paratrichodorus minor* (Stubby root nematode).

In a preferred embodiment, resistance to soybean sudden death syndrome (SDS) and/or infection with *Fusarium virguliforme* is increased by providing modified rhizobacteria.

The following examples are intended for illustration purposes only and are not intended to limit the invention in any way.

EXAMPLES

Example 1: Gibberellin-Deficient *B. japonicum* and Plant Growth

Figure 1B:

It has been shown that a number of rhizobacteria produce gibberellin plant hormones, including *B. japonicum*. The inventors previously identified the first enzymes involved in gibberellin biosynthesis in any rhizobacteria from *B. japonicum*, which further highlighted the presence of an associated collection of enzymatic genes in the *B. japonicum* genome that are almost certainly required for gibberellin production—i.e., a gibberellin biosynthetic operon. To investigate the role of such gibberellin production by *B. japonicum*, the inventors used a mutant strain of *B. japonicum* wherein CYP112 is no longer operational, generated by disrupting the first gene in this operon (CYP112) via insertion of an antibiotic resistance gene (FIG. 1). While this strain was originally constructed to simply demonstrate that the associated operon was required for gibberellin biosynthesis, it also provided the inventors with the means to test what role gibberellin production plays in the symbiotic relationship between soybean and *B. japonicum*. It has been suggested that such rhizobacterial production of gibberellin promotes host plant growth. However, the results do not show any difference between the biomass of plants nodulated with this insertional mutant strain versus wild-type *B. japonicum*. Nor were any effect on nodulation (e.g., number and size of nodules) observed, critically this included no change in the amount of nitrogen reduction carried out by the nodules containing the mutant versus the wild-type *B. japonicum*.

Example 2: Functional Conservation of the Capacity for Ent-Kaurene Biosynthesis and an Associated Operon in Certain Rhizobacteria Bacterial interactions with plants are accompanied by complex signal exchange processes. Previously, the nitrogen-fixing symbiotic rhizobacterium *B. japonicum* was found to carry adjacent genes encoding two sequentially acting diterpene cyclases that together transform geranylgeranyl diphosphate to ent-kaurene, the olefin precursor to the gibberellin plant hormones. Species from the three other major genera of rhizobacteria from the Rhizobiales order of the Alphaproteobacteria were found to have homologous terpene synthase genes. Cloning and functional characterization of a representative set of these enzymes confirmed the capacity of each genus to produce ent-kaurene. Moreover, comparison of their genomic context revealed that these diterpene synthases are found in a conserved operon which includes an adjacent isoprenyl diphosphate synthase, shown here to produce the geranylgeranyl diphosphate precursor, providing a critical link to central metabolism. In addition, the rest of the operon consists of enzymatic genes that presumably lead to a more elaborated diterpenoid, presumably the gibberellin $A_9$ that has been previously observed from bacteroids of B. japonicum. It has previously been shown that the operon is selectively expressed during nodulation, and the scattered distribution of the operon via independent horizontal gene transfer within the symbiotic plasmid or genomic island shown here suggests that such diterpenoid production may modulate the interaction of these particular symbionts with their host plants.

Materials and Methods

General.

Unless otherwise noted, all molecular biology reagents were purchased from Invitrogen and all other chemicals were from Fisher Scientific. B. japonicum USDA110 was obtained from Michael Sandowsky (University of Minnesota), and Mesorhizobium loti MAFF303099, Sinorhizobium fredii NGR234, and Rhizobium etli CFN42 were all obtained from Philip Poole (John Innes Centre), while Sinorhizobium meliloti 1021 was obtained from Kathryn Jones (Florida State University).

Escherichia coli was grown at 37 or 16° C. on either NZY (for cloning) or TB medium (for expression) Rhizobacteria were cultured with YEM medium at 28° C. When necessary, 1.8% agar was added to the relevant medium to pour plates. Where applicable, antibiotics were used at the following concentrations: chloramphenicol, 30 µg/ml; carbenicillin, 50 µg/ml; spectinomycin, 50 µg/ml; and kanamycin, 50 µg/ml. Liquid cultures were grown with vigorous shaking (200 rpm), generally in 250-ml Erlenmeyer flasks with 50 ml medium. Microanaerobic cultures were grown in YEM medium with 10 mM $KNO_3$ under an atmosphere of nitrogen gas ($N_2$) and ~0.5% oxygen with moderate shaking (80 rpm) in rubber-stoppered flasks, with the atmosphere exchanged every 12 h ($N_2$ was blown into the flasks for 15 min).

Sequence Retrieval and Analysis.

All sequences were retrieved from the National Center for Biotechnology Information (NCBI) website. The amino acid sequence of the previously characterized KS from B. japonicum (BjKS) was used as a query for BLAST searches against the Rhizobiales order (i.e., by restricting the search to this order, defined as taxid 356) on the NCBI website. This also was done using the amino acid sequence of CPS from B. japonicum (BjCPS) as the query sequence. Sequence analyses were carried out with the CLC Main Workbench program (version 6.8.4). Alignments used the following parameters: gap open cost, 10; gap extension cost, 10; and end gap cost, as any other. Trees were prepared using the neighbor-joining algorithm with a bootstrap analysis of 1,000 replicates. PAUP analysis was used to confirm the topology of the resulting trees. The phylogenetic analyses whose results are presented here were carried out using genes encoding biochemically analogous proteins from a bacterial species as distantly related as possible as the designated outgroup sequence. For CPS, this was from Streptomyces sp. strain KO-3988, which falls within the Actinobacteria phylum, yet this Streptomyces sp. CPS (Ss-CPS) (GenBank accession number AB183750) also produces ent-CPP. For NifK, this was from Azotobacter vinelandii (AvNifK; GenBank accession number Avin_01400), which falls within the Proteobacteria phylum but is in the distinct Gammaproteobacteria class.

Cloning and Characterization of CPS and KS.

Genomic DNA was isolated from rhizobacteria using a Generation capture kit (Qiagen) following the manufacturer's protocol. Each CPS and KS gene was amplified via PCR from genomic DNA using gene-specific primers and cloned into pENTR-SD-dTOPO (Invitrogen). Biochemical characterization of the CPS-KS pair from each species of rhizobacteria was carried out as described previously for B. japonicum. Briefly, the KS genes were subcloned into the plasmid pGG-DEST, which carries a plant GGPP synthase (GGPS), and the CPS genes were subcloned into pDEST14. This enabled use of a previously described metabolic engineering system, which included constructs analogous to the CPS and KS from Arabidopsis thaliana. Accordingly, the E. coli strain OverExpress C41 (Lucigen) was transformed with the various combinations of the pGG-DEST::CPS and pDEST14::KS plasmids described below, along with pIRS (i.e., to increase the isoprenoid precursor pool, as described previously). Liquid cultures (50 ml) of the resulting recombinant E. coli strains were induced at an optical density at 600 nm of 0.6, the pH was adjusted to 7.1, and the bacteria were grown at 16° C. for 72 h. The cultures were then extracted with an equal volume of hexanes. The organic extract was separated out and dried in a rotary evaporator, and the residue was resuspended in 100 µl hexanes. This concentrated extract was analyzed by gas chromatography (GC), carried out on a Varian (Palo Alto, Calif.) 3900 GC with a Saturn 2100 ion trap mass spectrometer (MS) in electron ionization (70 eV) mode. Samples (1 µl) were injected in splitless mode at 50° C., and after holding for 3 min at 50° C., the oven temperature was raised at a rate of 14° C./min to 300° C., where it was held for an additional 3 min. MS data from m/z 90 to 600 were collected starting 12 min after injection and were collected until the end of the run. The production of ent-kaurene was verified by comparison of the mass spectra and retention time to those of an authentic standard (enzymatically produced by the characterized CPS and KS from A. thaliana).

Mapping the Diterpenoid Biosynthesis Operon.

A 20-kb region surrounding each biochemically characterized KS was downloaded from the NCBI website and further analyzed. The predicted genes that either were homologous to those in the B. japonicum operon or had plausible predicted functions in (di)terpenoid biosynthesis were identified by alignment and open reading frame prediction. In each case, the boundaries of each operon were clear from the predicted functions of the adjacent genes (i.e., these have no plausible function in terpenoid biosynthesis). Putative RpoN and NifA binding sites were identified by searching for identical matches in the upstream region of each operon to previously defined 16-nucleotide motifs.

Characterization of GGPS.

Fragments from the 5' end of the operon from S. fredii, including genes for GGPS-CPS-KS or CPS-KS only, were amplified from genomic DNA via PCR. These were cloned into pZeroBlunt and then subcloned into a previously described S. meliloti overexpression vector, pstb-LAFR5, using BamHI and EcoRI restriction sites introduced by PCR, along with three upstream stop codons and an optimized ribosome binding site. The resulting constructs were transformed into *S. meliloti* 1021 by triparental mating using *E. coli* strain MM294A carrying the construct and *E. coli* strain MT616 as the helper, as described previously. These recombinant strains were grown for 5 days, and then the total culture was extracted with an equal volume of hexanes. This organic extract was separated out and dried under a gentle stream of $N_2$, with the residue then resuspended in 200 µl of hexanes for analysis by GC-MS, as described above.

Analysis of Rhizobacterial Diterpenoid Production.

Liquid cultures grown under aerobic or microanaerobic conditions were harvested 3, 6, or 9 days after inoculation, and the cells were separated from the spent medium by centrifugation (15 min at 10,000 g). For analysis of the gibberellin content, the supernatant was acidified to pH 2.5 with acetic acid and then extracted with an equal volume of ethyl acetate saturated with acetic acid (1%, vol/vol). This organic extract was separated and passed over a 1-ml HP-20 resin column, which was then eluted with 3 ml each of 1% acetic acid in distilled $H_2O$ ($dH_2O$) and 40% and 80% (vol/vol in $dH_2O$ with 1% acetic acid) methanol. Each of these fractions was dried in a rotary evaporator, and the residue was resuspended in 100 µl acetic acid-saturated ethyl acetate for analysis by GC-MS as described above. For analysis of the ent-kaurene intermediate, the total culture was directly extracted with an equal volume of hexanes, which was separated out and passed over a 1-ml silica gel column to remove contaminating polar compounds. The resulting organic extract was dried under a gentle stream of $N_2$, and the residue was resuspended in 100 µl of hexanes for analysis by GC-MS, again, as described above.

Results

Identification of KS and CPS Homologs in Rhizobacteria.

As noted above, the BjKS that directly produces ent-kaurene exhibits distinct sequence homology relative to other characterized bacterial diterpene synthases. Accordingly, the BjKS sequence was used in initial BLAST searches of the NCBI database to identify bacteria from the Rhizobiales order that contain homologous diterpene synthases. Notably, homologs were found in species from all four major genera of rhizobacteria, i.e., *Rhizobium, Sinorhizobium,* and *Mesorhizobium*, in addition to *Bradyrhizobium*. In each case, immediately upstream of the BjKS homolog was a homolog to BjCPS (Table 1) with 4-nucleotide-overlapping open reading frames, just like the 4-nucleotide-overlapping open reading frame found in *B. japonicum*. Interestingly, these were not conserved by bacterial phylogeny; e.g., the KS from the various species of *Bradyrhizobium* shared less sequence identity than BjKS and the KS from *Mesorhizobium loti*, which not only is in a distinct genus but also falls into the separate Phyllobacteriaceae family. Accordingly, KS and CPS appear to have been distributed via horizontal gene transfer. Consistent with such an inheritance mechanism, the KS gene is not found in all rhizobacteria (e.g., no homolog is present in *Rhizobium leguminosarum*, whose genome has been fully sequenced, nor are homologs present in any of the genome sequences reported for various strains of *S. meliloti*, despite the presence of a homologous protein sequence annotated as being encoded by *Sinorhizobium meliloti*.

TABLE 1

Homologues of *B. japonicum* kaurene synthase (KS) and copalyl diphosphate synthase (CPS) in other rhizobacteria.

| Organism | KS GenBank accession no. | % identity to BjKS | CPS GenBank accession no. | % identity to BjKS |
|---|---|---|---|---|
| *Bradyrhizobium japonicum* | NP_768790 | | NP_768789 | |
| *Bradyrhizobium elkanii* | WP_018270013 | 91 | WP_016845990 | 92 |
| *Bradyrhizobium* sp. strain WSM1253 | WP_007600190 | 89 | WP_007600189 | 91 |
| *Bradyrhizobium* sp. strain WSM471 | WP_007605894 | 88 | WP_007605892 | 91 |
| *Mesorhizobium loti* | NP_106894 | 93 | NP_106893 | 93 |
| *Mesorhizobium alhagi* | WP_008838313 | 94 | WP_008838314 | 95 |
| *Mesorhizobium amorphae* | WP_006204703 | 93 | WP_006204702 | 93 |
| *Mesorhizobium ciceri* | YP_004144785 | 92 | YP_004144784 | 92 |
| *Mesorhizobium* sp. strain STM 4661 | WP_006329103 | 92 | WP_006329109 | 93 |
| *Mesorhizobium* sp. Strain WSM4349 | WP_018457688 | 92 | WP_018457687 | 93 |
| *Sinorhizobium fredii* | NP_443948 | 92 | NP_443949 | 95 |
| *Sinorhizobium meliloti* | WP_018098888 | 91 | WP_018098887 | 94 |
| *Sinorhizobium medicae* | WP_018009727 | 90 | WP_018009726 | 92 |
| *Rhizobium etli* | NP_659792 | 87 | NP_659791 | 86 |
| *Rhizobium tropici* | YP_007335933 | 87 | YP_007335932 | 90 |
| *Rhizobium* sp. Strain CCGE 510 | WP_007636919 | 88 | WP_007636921 | 87 |
| *Rhizobium grahamii* | WP_016558477 | 71 | WP_016558476 | 72 |
| *Rhizobium mesoamericanum* | WP_007539161 | 69 | WP_007539159 | 72 |

Functional Characterization of Representative CPSs and KSs.

To investigate the ability of the CPS and KS homologs found in our bioinformatics search to cooperatively produce ent-kaurene, the Inventors analyzed these from one species from each genus, specifically, examples of species for which complete genome sequences have been reported, *Mesorhizobium loti* MAFF303099, *Sinorhizobium fredii* NGR234, and *Rhizobium etli* CFN42. The Inventors cloned and characterized the CPS and KS from each of these species much as previously described for those from *B. japonicum*. Briefly, each pair of CPS and KS homologs was coexpressed in recombinant *E. coli* also expressing a plant GGPP synthase (GGPS), which led to the production of kaurene (FIG. 4). To demonstrate stereospecificity, each CPS was expressed in recombinant *E. coli* with the plant GGPS and KS from *Arabidopsis thaliana* (AtKS), which is specific for ent-CPP. In addition, each KS was expressed in recombinant *E. coli* with the plant GGPS and ent-CPP-producing CPS from *Arabidopsis thaliana* (AtCPS). In each case, this led to the production of ent-kaurene (data not shown), demonstrating a stereochemistry consistent with that of the gibberellin plant hormones. These results confirmed a common catalytic activity for these distributed enzymatic genes and, importantly, that each genus identified here contains the capacity to produce ent-kaurene from GGPP.

Defining a Rhizobacterial Diterpenoid Biosynthetic Operon.

Given that the genes for BjCPS and BjKS are neighboring genes in what has been proposed to be a more extensive operon, the Inventors examined the genomic context for each of the characterized CPSs and KSs to determine if these were similarly set in a more broadly conserved operon. Indeed, homologs to all of the other genes from the *B. japonicum* operon also were present, with retention of relative gene order. In particular, homologs to the cytochromes P450 CYP112 and CYP114, a ferredoxin (Fd), a short-chain alcohol dehydrogenase/reductase (SDR), another cytochrome P450 (CYP117), an isoprenyl diphosphate synthase that presumably makes GGPP (GGPS), as well as the orthologous CPS and KS were detected. Although it should be noted that some of these genes were fused together in certain cases (i.e., the CYP114 and Fd in *R. etli* and the Fd and SDR in *M. loti*) these still exhibited clear homology to the separate genes found elsewhere. Thus, these genes define a core diterpenoid biosynthetic gene cluster/operon that is conserved across all four of the major rhizobacterial genera, sharing 80 to 92% nucleotide sequence identity.

Figure 5:
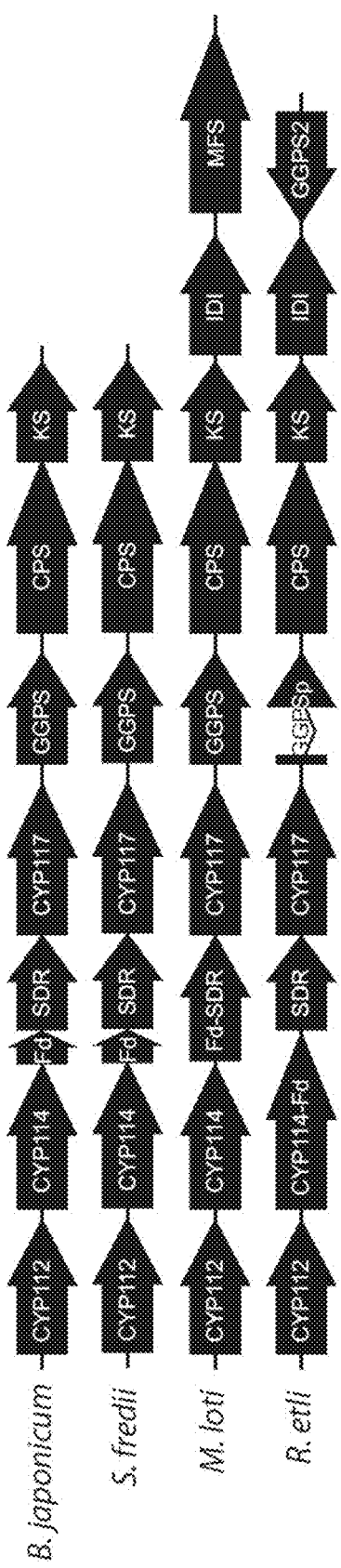
FIG. 5 shows a schematic of diterpenoid biosynthesis operon from the designated rhizobacteria. Homologs to the cytochromes P450 CYP112 and CYP114; ferredoxin (Fd); short-chain alcohol dehydrogenase/reductase (SDR); another cytochrome P450 (CYP117); isoprenyl diphosphate (GGPP) synthase (GGPS); orthologous copalyl diphosphate synthase (CPS) and kaurene synthase (KS).

Notably, the GGPS gene in *R. etli* appears to be disrupted. While some homologous sequence is present, there is a large internal deletion, resulting in a clearly compromised open reading frame (accordingly, the Inventors suggest that this is a pseudogene and refer to it as GGPSp). However, *R. etli* contains another isoprenyl diphosphate synthase in close proximity to its core operon. Although this is not closely related to the GGPS found within the operon and is in the opposite orientation, the Inventors hypothesize that this might serve the same function (and refer to it here as GGPS2). There is an intervening gene. However, this gene appears to encode an isopentenyl diphosphate isomerase (IDI), which balances isoprenoid precursor supply and, thus, similarly has a plausible role in (di)terpenoid biosynthesis as well. Further analysis demonstrated that a homologous IDI gene also occurs at the same position (3' to the KS) in *M. loti*. Intriguingly, *M. loti* further has a gene encoding a major facilitator superfamily (MFS) member immediately downstream of its IDI, and the Inventors speculate that this might be involved in secretion of the final diterpenoid natural product. Accordingly, in *R. etli* and *M. loti*, accessory genes appear to have been appended to the core diterpenoid biosynthesis operon (FIG. 5).

Upon sequence comparisons of the core operon, that from *R. etli* appeared to be the most divergent, sharing <82% identity, while the others were ≥90% identical to each other. Even when excluding the compromised GGPSp, comparison of the other genes from the *R. etli* operon revealed that these are only 86 to 89% identical to those from the other rhizobacteria, which is less than the level of identity shared by the other rhizobacteria. Accordingly, the *R. etli* operon is clearly the most divergent, consistent with distribution of the entire operon by horizontal gene transfer; e.g., despite their common phylogenetic origin in the Rhizobiaceae family, *R. etli* and *S. fredii* contain the most disparate rhizobacterial diterpenoid biosynthesis operons.

Demonstrating Production of GGPP and Capacity for Ent-Kaurene Production.

Figure 6:
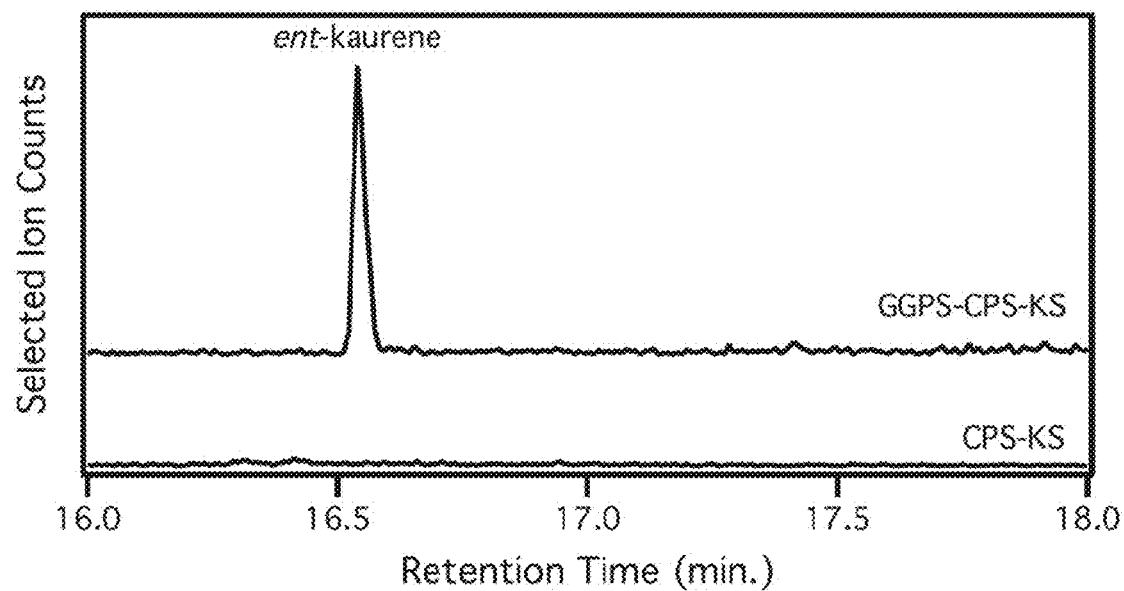
FIG. 6 shows selected ion (m/z 272) chromatograms obtained by GC-MS demonstrating production of ent-kaurene from *S. meliloti* 1021 expressing GGPS-CPS-KS, but not CPS-KS alone, from *S. fredii* NGR234 (as indicated).
Figures 7A, 7B:
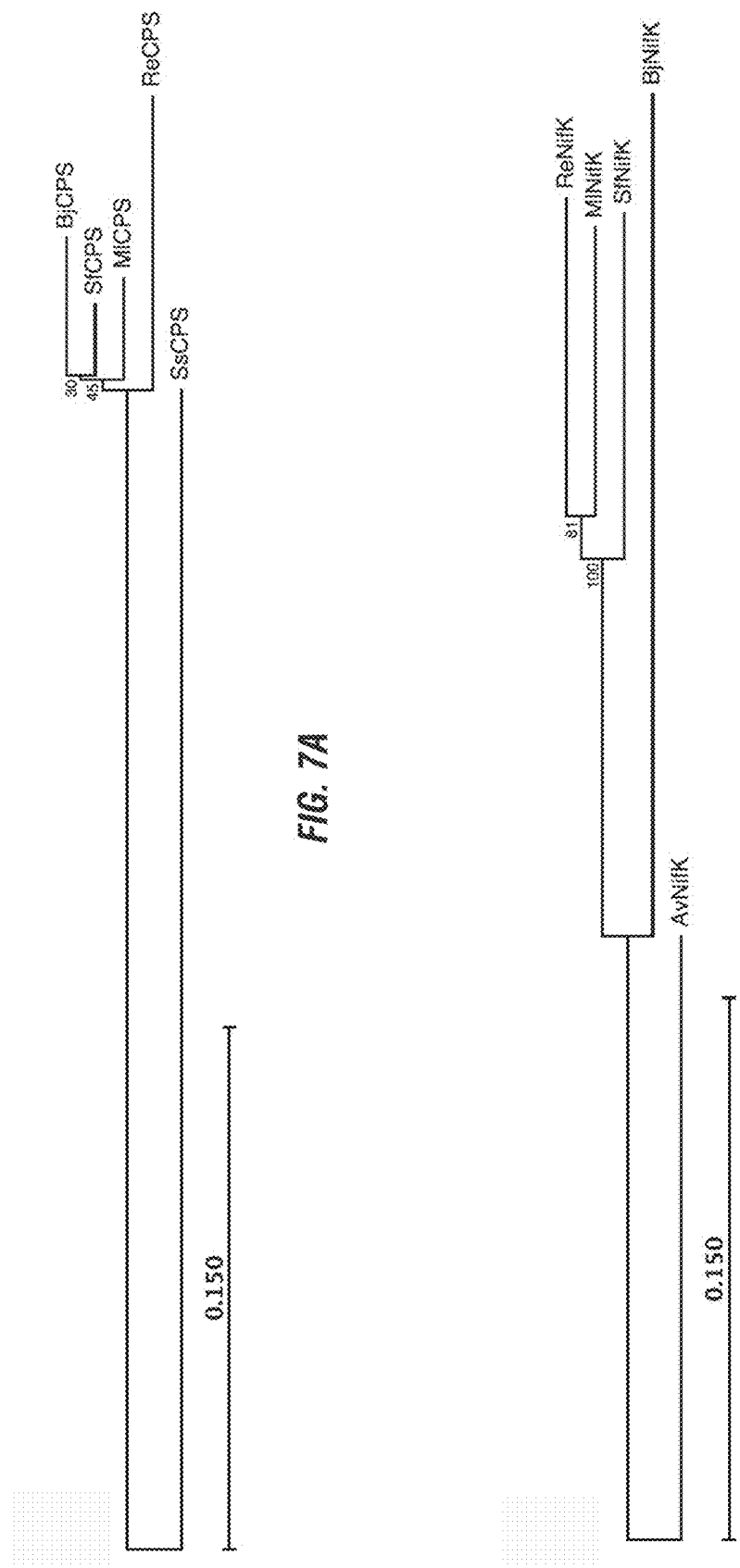
FIG. 7(A-B) shows molecular phylogenetic analysis of rhizobacterial genes. (A) shows analyais for the characterized rhizobacterial CPS genes. (B) shows analysis for the nitrogenase subunit NifK genes from the same rhizobacteria. SsCPS and AvNifK are the designated outgroup sequences, as described in the text. SfCPS, *S. fredii* CPS; MlCPS, *M. loti* CPS; ReCPS, *R. etli* CPS; ReNifK, *R. etli* NifK; MlNifK, *M. loti* NifK; SfNifK, *S. fredii* NifK; BjNifK, *B. japonicum* NifK.

Diterpenoid biosynthesis generally proceeds via the initial formation of a hydrocarbon skeletal structure, followed by oxidative elaboration. In the organization of the rhizobacterial diterpenoid biosynthesis operons, it is notable that the genes predicted to be involved in oxidation are in the 5' region, with all those predicted to be involved in the formation of the cyclized olefin ent-kaurene falling in the 3' region. This includes the putative GGPP synthase (GGPS), as bacteria do not necessarily produce GGPP, leading to the presence of a GGPS in all of the identified bacterial diterpenoid biosynthetic gene clusters. The observed organization of the rhizobacterial diterpenoid biosynthetic operon suggests that the 3' and 5' regions might form nominally independent subclusters, although no such subclusters appear in the currently available sequence information. Nevertheless, the Inventors took advantage of this gene arrangement to demonstrate both the production of GGPP by the isoprenyl diphosphate synthase and, hence, the ability of the operon to lead to the production of at least ent-kaurene. In particular, while initial efforts were directed at heterologous expression of the putative GGPP synthase in *E. coli* for use in coexpression studies such as those described above, that ultimately proved unsuccessful. The Inventors then turned to recombinant expression in a more closely related bacterium, specifically, the 1021 strain of *Sinorhizobium meliloti*, whose reported genome sequence does not contain the rhizobacterial diterpenoid biosynthesis operon. Accordingly, the Inventors overexpressed the 3' region of the operon from the closely related *S. fredii*, either a fragment containing GGPS-CPS-KS or a fragment containing CPS-KS only. Consistent with the usual lack of GGPP production in bacteria, expression of the CPS-KS genes alone in *S. meliloti* 1021 did not result in the production of ent-kaurene, while expression of the GGPS-CPS-KS genes did (FIG. 6). These results, then, confirm that the associated isoprenyl diphosphate synthase produces GGPP, providing a critical link to central metabolism, and further demonstrate the capacity of the operon to confer the ability to produce at least ent-kaurene.

Discussion

These results demonstrate a scattered distribution of a diterpenoid biosynthetic operon within the rhizobacteria, with functional conservation of at least the capacity for the production of ent-kaurene (FIGS. 4 and 6). Indeed, more recent bioinformatics searches have revealed the presence of a homologous operon in *Burkholderia* sp. JPY251, a rhizobacteria from the separate Betaproteobacteria class. The location of this operon in the symbiotic module of the relevant rhizobacteria, along with its previously demonstrated transcription in response to bacteroid differentiation in nodules, indicates a putative role for the resulting diterpenoid natural product in the symbiotic relationship of these rhizobacteria with their host plants. Further, the scattered distribution of the operon, which appears to be a result of its apparently independent horizontal gene transfer between symbiotic nodules, suggests that it provides a selective advantage only under certain conditions. Nevertheless, the striking conservation of this diterpenoid biosynthetic operon hints at its importance. Intriguingly, all the characterized operons are from rhizobacteria associated with determinate, rather than indeterminate, nodules. While nodule type is specified by the host plant species, rhizobacterial specificity for plant host species indirectly controls bacterial nodulation phenotypes. Accordingly, it appears that the diterpenoid product of this operon, most likely the gibberellin $A_9$ that has recently been shown to be produced by bacteroids of *B. japonicum*, specifically plays a role in rhizobacterial interactions within determinate nodules. In addition, there are examples of the operon found in rhizobacteria usually isolated from plants that form indeterminate nodules (e.g., *S. meliloti*), suggesting that bacterial gibberellin production may play a role in these plant-microbe interactions as well.

Example 3: Gibberellin Production by Other Bacteria

Figure 2A:
FIG. 2 (A-C) shows that a gibberellin deficient mutant strain of *X. oryzae* exhibits reduced virulence, as measured by both lesion length (A) and number of bacteria (B; CFU=colony forming units). The gibberellin locus in *X. oryzae* is depicted in (A) with the knocked-out gene (CPS) crossed out.
Figure 2B:
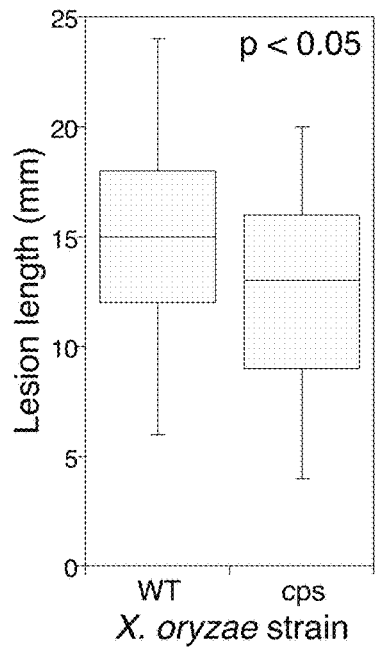
Figure 2C:
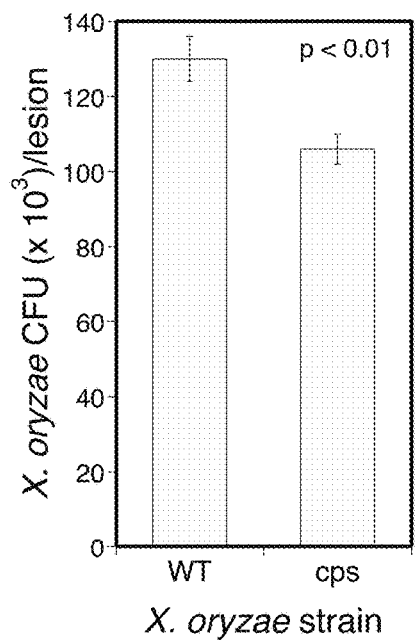

Besides being found in the genomes of other rhizobacteria, the gibberellin biosynthesis operon also can be found in the genome of plant pathogens such as the rice leaf blight agent *Xanthomonas oryzae* pv. *oryzicola* (Xoc). Rice is a cereal grain, not a nodulating plant, and Xoc is a pathogen, not a nodulating bacteria. The inventors have previously shown that at least the genes characterized from *B. japonicum* retain the same biochemical function in Xoc. In addition, the inventors have generated knock-outs of these genes in Xoc, again primarily to demonstrate their specific function in gibberellin biosynthesis, but also to investigate the role of gibberellin production by this phytopathogen. It has been shown that rice plants that are defective in gibberellin metabolism exhibit increased disease resistance, although these further have the expected decreases in stature—i.e., because the gibberellins promote plant growth and development. Critically, the application of gibberellins also decreases rice disease resistance. Thus, the Inventors hypothesized that the production of gibberellins by Xoc might serve to suppress the host rice plant defense response—i.e., as a virulence factor for this phytopathogen. Indeed, the Inventors found that the strains of Xoc in which genes from the gibberellin biosynthetic operon have been disrupted do exhibit reduced virulence, both in lesion size, as well as numbers of bacteria, demonstrating that at least Xoc produces gibberellins as a virulence factor (FIG. 2).

Figure 3A:
FIG. 3 (A-C) shows that nodulation by a gibberellin-deficient mutant (A) strain of *B. japonicum* (cyp112) leads to similar numbers and size of root nodules (B) but the nodules formed contain fewer viable bacteria (C; CFU). Nodulation by the gibberellin-deficient mutant does not affect the number, size, or nitrogen fixing capacity.
Figure 3B:
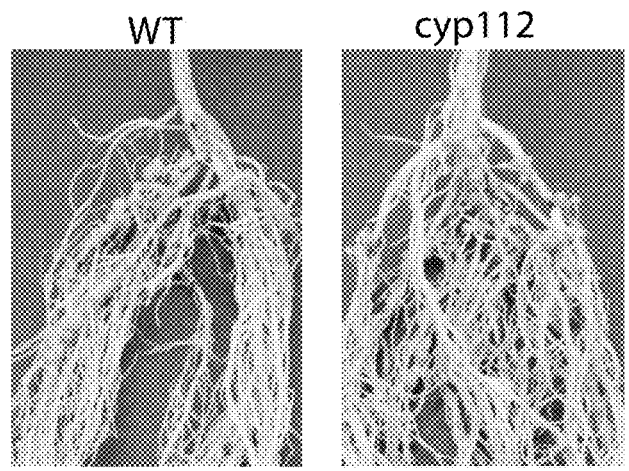
Figure 3C:
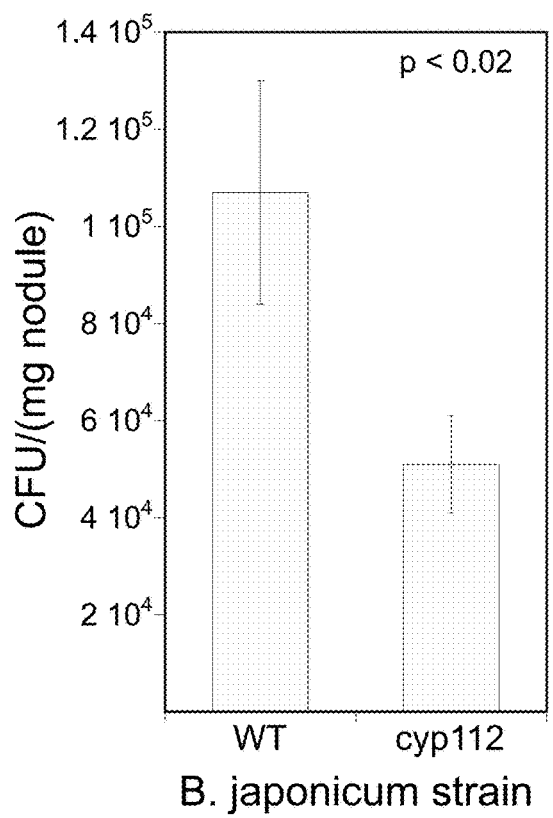
Figure 4A:
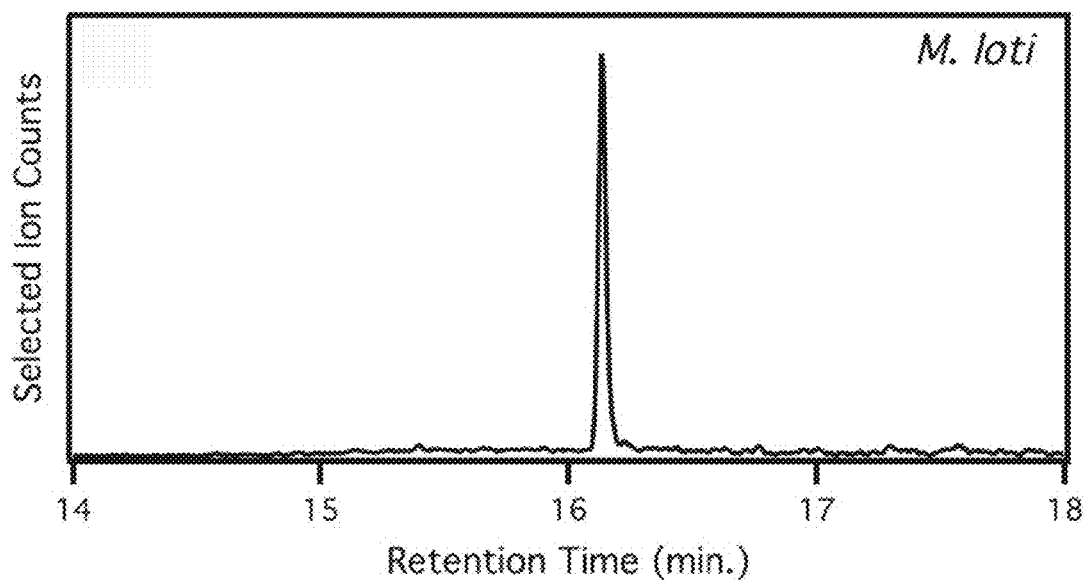
FIG. 4 (A-D) shows selected ion (m/z 272) chromatograms obtained by GC-MS demonstrating production of ent-kaurene from GGPP by coexpressing CPS and KS from various rhizobacteria. (A) *M. loti*, (B) *S. fredii*, and (C) *R. etli*, along with (D) an authentic standard (from coexpression of the CPS and KS from *Arabidopsis thaliana*) in *E. coli* (along with a GGPP synthase).
Figure 4B:
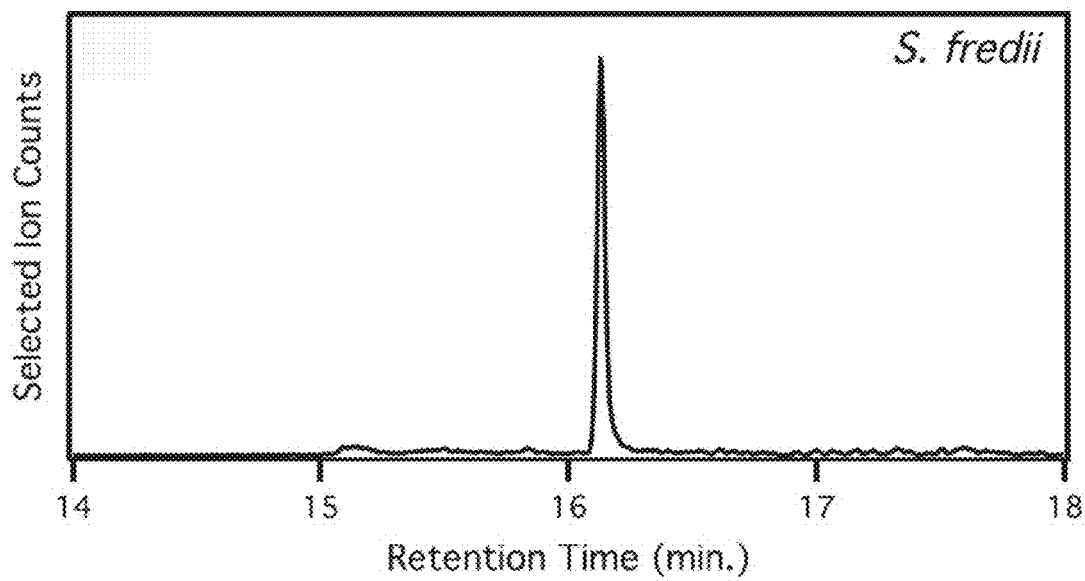
Figure 4C:
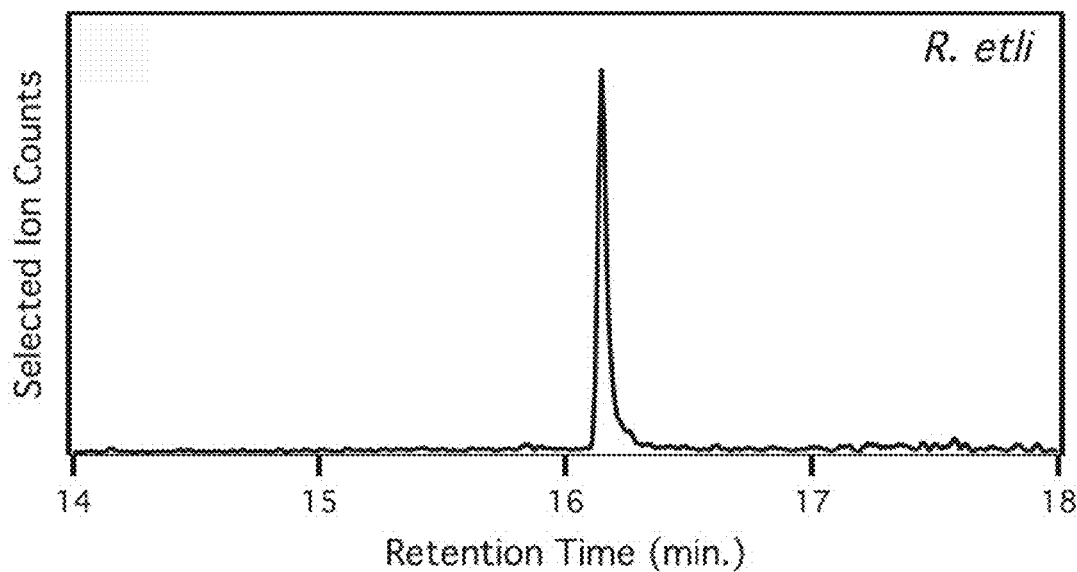
Figure 4D:
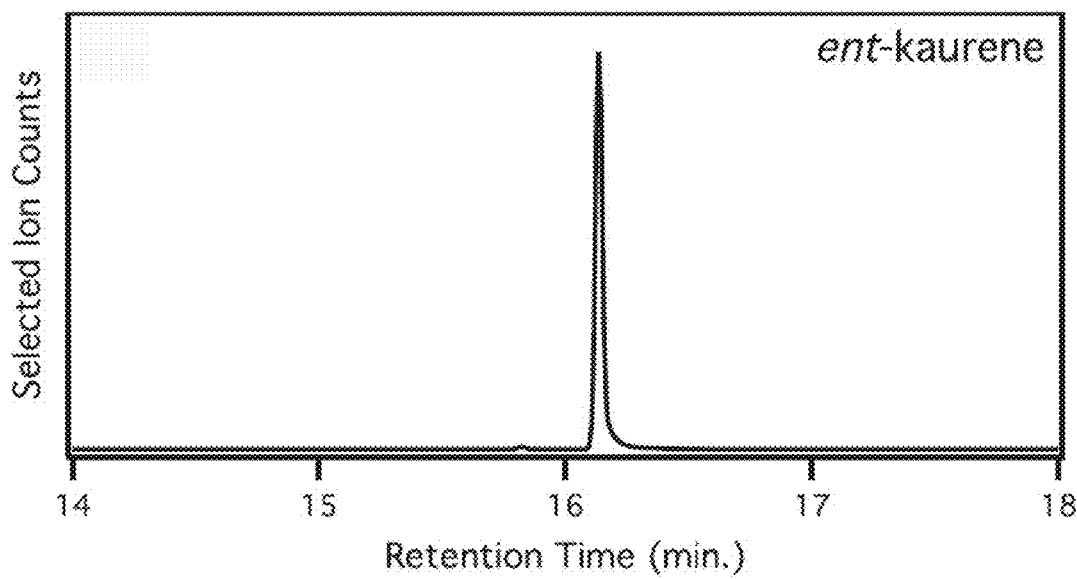

Example 4: Mutant Plants have Normal $CO_2$ Assimilation Rates Under Ambient $pCO_2$ Based on the results obtained with Xoc, the Inventors determined that *B. japonicum* produces gibberellins to suppress the soybean defense response, rather than promote plant growth other than that of the nodules in which *B. japonicum* is located. Strikingly, there was a significant decrease in the number of viable bacteria from nodules containing the mutant strain (in which CYP112 was disrupted) relative to those containing wild-type *B. japonicum* (FIG. 3). Given that these nodules carry out the same amount of nitrogen reduction and, therefore, must contain similar numbers of bacteria, these results indicate that the mutant strain of *B. japonicum* has been terminally differentiated into bacteroids. These results demonstrate that soybeans can mount the typical legume plant defense response against nodulating rhizobacteria, but that *B. japonicum* produces gibberellins to suppress soybeans' ability to force such terminal differentiation.

Example 5: Gibberellin-Deficient Rhizobacteria Promote Enhanced Resistance to Soybean Sudden Death Syndrome (SDS)

Based on the results demonstrating that *B. japonicum* produces gibberellins to suppress the soybean defense response, the inventors assessed the ability of plants inoculated with *B. japonicum* with lacking gibberellin production to resist infection.

Sudden death syndrome (SDS) in soybeans is caused by soil-borne fungi within a group (clade 2) of the *Fusarium solani* species complex (Aoki et al., 2003; Aoki et al., 2005). In North America, *Fusarium virguliforme* is the causal agent. The SDS pathogen survives between soybean crops as chlamydospores in crop residue or freely in the soil. The thick-walled chlamydospores develop in the soil and on soybean roots during disease development and thereafter. Chlamydospores can withstand wide fluctuations in soil temperature, including freezing, and resist desiccation. As soil warms in the spring, chlamydospores near soybean roots are stimulated to germinate, and then infect soybean roots.

The fungus may infect roots of soybean seedlings soon after planting, but above ground symptoms of SDS generally appear after the soybean plants have reached reproductive stages. The fungus produces toxins in the roots that are translocated to the leaves and cause foliar symptoms; the fungus itself does not invade the stems more than a few centimeters above the soil line. Early symptoms of SDS include yellowing and defoliation of upper leaves. Symptoms may initially be confined to a few small areas or strips in the field, but over the following two or three weeks, affected areas may enlarge and plants in other areas in the field may exhibit symptoms. The extent of yield losses due to SDS depends on the severity and timing of disease expression relative to plant development in regards to yield components. If the disease develops early in the season, flowers and young pods will abort. When the disease develops later, the plant will produce fewer seeds per pod or smaller seeds. The earlier severe disease develops, the more the yield is reduced. Due to the persistence of *F. virguliform* and the potential severity of disease, methods and compositions providing increased resistance to infection would be agriculturally advantageous and beneficial. Accordingly, the inventors sought to determine whether providing gibberellin-deficient *B. japonicum* to plants would enhance the plant's resistance to *F. virguliform* infection and development of SDS disease.

Individual soybean plants were inoculated with wild-type (USDA 110) or gibberellin-deficient *B. japonicum*. Vegetative and flowering plants were inoculated by transplantation into soil infested with *F. virguliforme* (a 30:1 mixture of soil and sorghum grains infected with *F. virguliforme*). Flowering plants were roughly 4 weeks old and in their 4th-5th trifoliate at the time of transplanting, while young (vegetative) plants were 2 weeks old and in their 2nd trifoliate. Flowering plants from the same germination and *B. japonicum* inoculation dates were confirmed to be nodulated with the correct strain of *B. japonicum*, although nodules were not easily visible on the younger plants. Non-transplanted soybean plants that were germinated on the same date remained green and healthy, strongly suggesting that nodulation was successful. Plants were grown under a diurnal cycle consisting of 16 hours of light at 24° Celsius, and 8 hours of dark at 18° Celsius.

Plant measurements were taken starting 13 days after transplanting into infested soil. Flowering plants had produced their 5th trifoliate when measurements were initially taken, while young (vegetative) plants were between their 2nd and 3rd trifoliate stage. Three plants from each treatment (nodulation with wild-type or gibberellin-deficient *B. japonicum*) and stage of life cycle at infection (flowering or vegetative) were assessed for disease symptoms, as determined by percentage of discolored leaf surface. Measurements also were taken at 19 and 67 days after transplanting, although data for the 6th trifoliate is only presented for the 19 day post transplantation assessment as these leaves were not yet present at the 13 day time point, and had fallen off the plants nodulated with wild-type, but not gibberellin-deficient *B. japonicum*.

Figure 8:
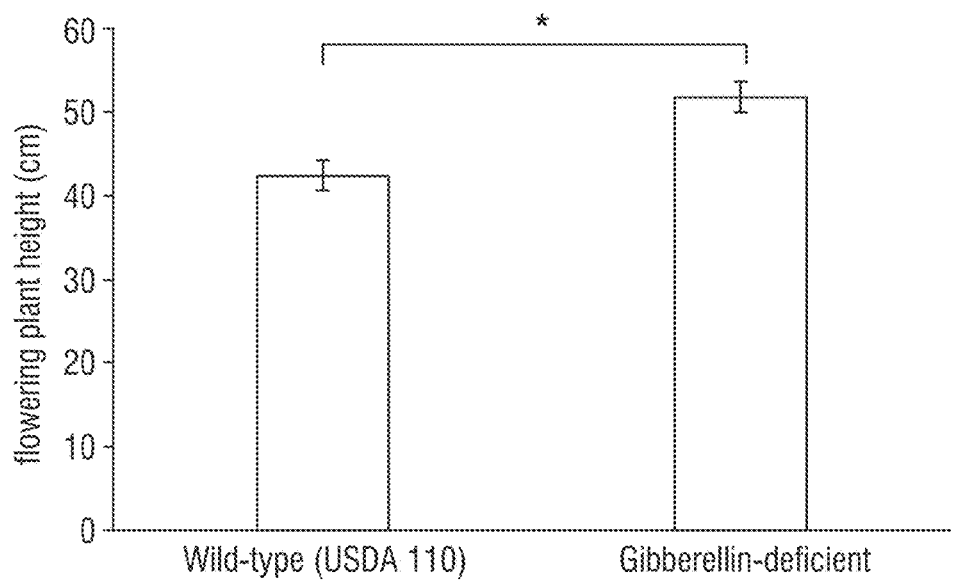
FIG. 8 shows nodulating plants inoculated with gibberellin-deficient rhizobacteria according to one embodiment of the invention exhibit increased growth compared to plants inoculated with gibberellin-sufficient rhizobacteria. Flowering soybean plants were inoculated with wild-type *B. japonicum* (USDA 110) or modified, gibberellin-deficient *B. japonicum*. Height was measured approximately 7 weeks after planting.
Figure 9:
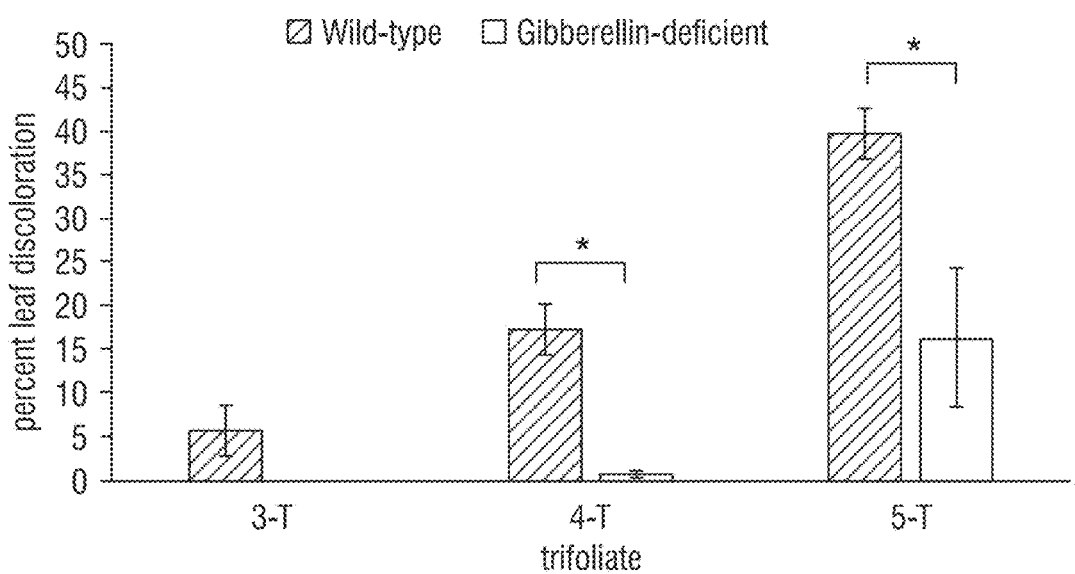
FIG. 9 shows reduced disease symptoms in plants inoculated with gibberellin-deficient rhizobacteria compared to plants inoculated with gibberellin-sufficient rhizobacteria. Flowering plants inoculated with wild-type (USDA 110) or modified, gibberellin-deficient *B. japonicum* were assessed for percentage of leaf surface that was discolored at 13 days after exposure to *F. virguliforme* (6 weeks following planting). Measurements were made at the third, fourth, and fifth trifoliates.
Figure 10:
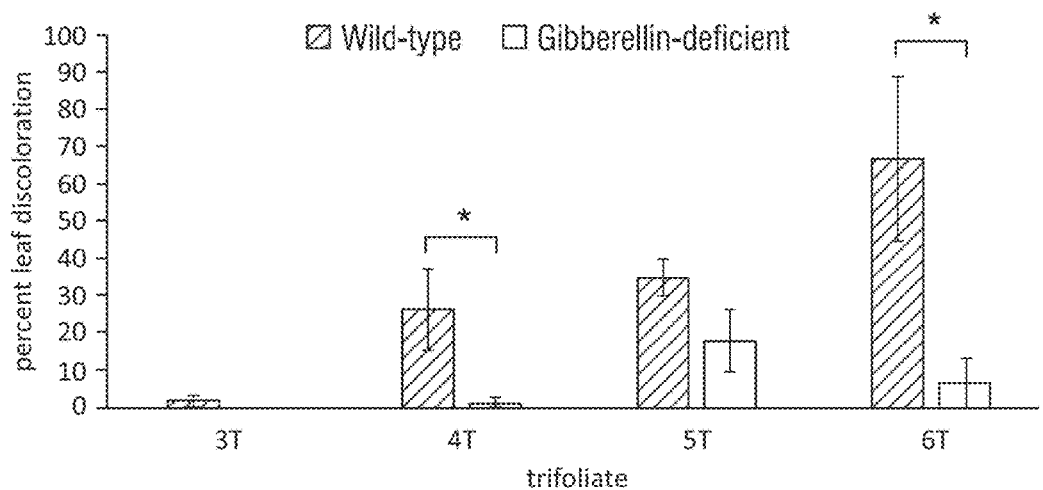
FIG. 10 shows reduced disease symptoms in plants inoculated with gibberellin-deficient rhizobacteria compared to plants inoculated with gibberellin-sufficient rhizobacteria. Flowering plants inoculated with wild-type (USDA 110) or modified, gibberellin-deficient *B. japonicum* were assessed for percentage of leaf surface that was discolored at 19 days after exposure to *F. virguliforme* (7 weeks following planting). Measurements were made at the third, fourth, fifth, and sixth trifoliates.
Figure 11:
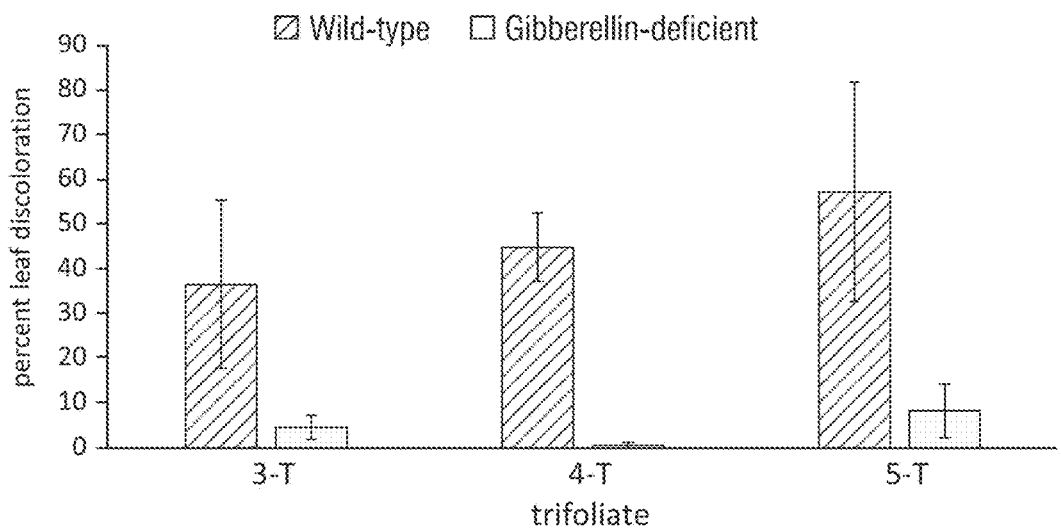
FIG. 11 shows reduced disease symptoms in plants inoculated with gibberellin-deficient rhizobacteria compared to plants inoculated with gibberellin-sufficient rhizobacteria. Flowering plants inoculated with wild-type (USDA 110) or modified, gibberellin-deficient *B. japonicum* were assessed for percentage of leaf surface that was discolored at 67 days after exposure to *F. virguliforme* (14 weeks following planting). Measurements were made at the third, fourth, and fifth trifoliates (the leaves of the sixth trifoliate had fallen off in the plants that had been nodulated with wild-type, although not modified, gibberellin-deficient *B. japonicum*).
Figure 12A:
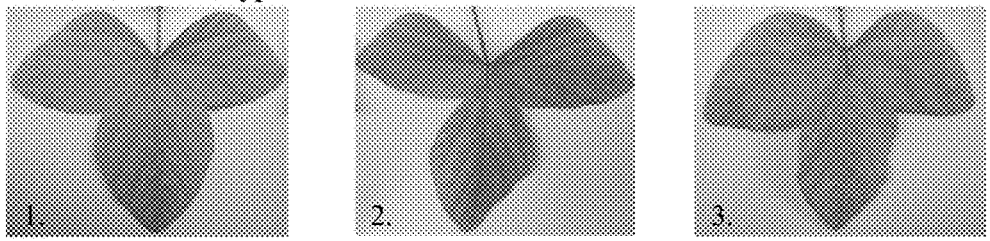
FIG. 12 (A-D) shows reduced disease symptoms in plants inoculated with gibberellin-deficient rhizobacteria compared to plants inoculated with gibberellin-sufficient rhizobacteria. The 3rd (A), 4th (B), 5th (C), and 6th (D) trifoliates of flowering soybeans inoculated with either wild-type (USDA 110) or gibberellin-deficient *B. japonicum* were photographed at 19 days after exposure to *F. virguliforme* (7 weeks following planting). Three replicates of each are shown (labeled 1-3).
Figure 12A:
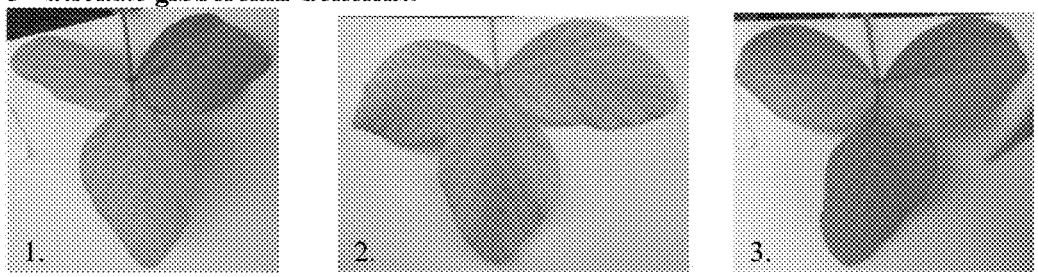
Figure 12B:
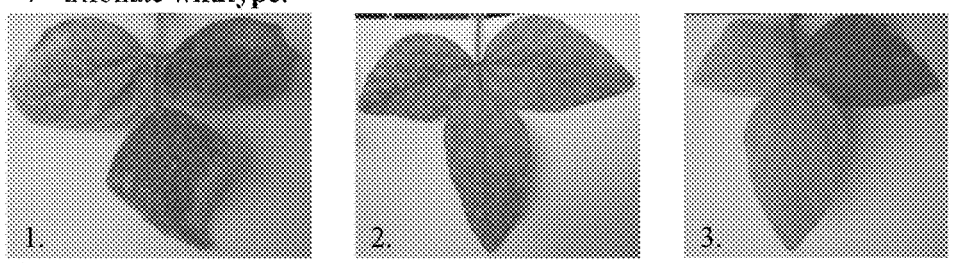
Figure 12B:
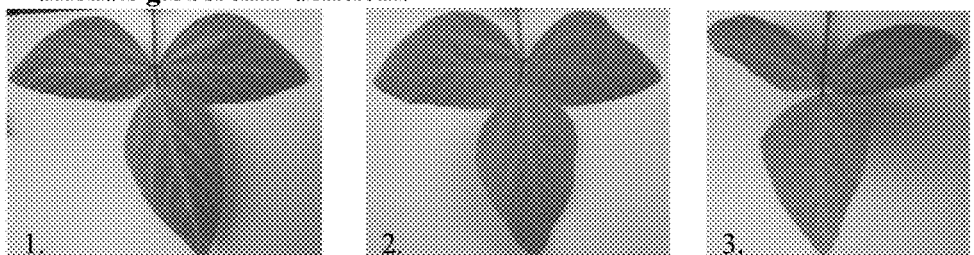
Figure 12C:
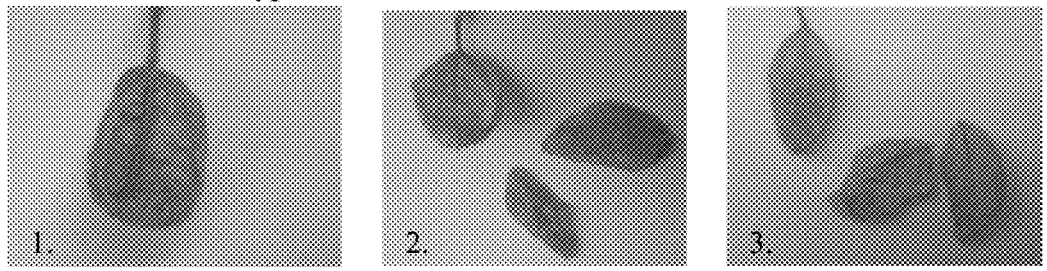
Figure 12C:
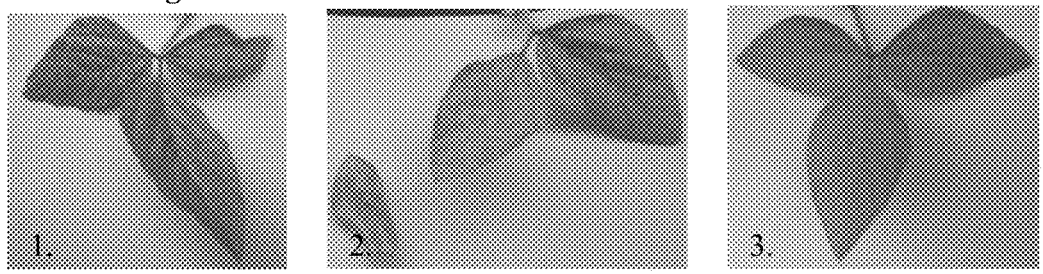
Figure 12D:
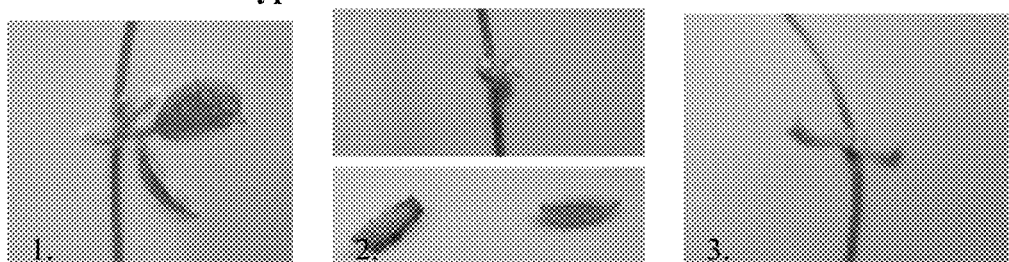
Figure 12D:
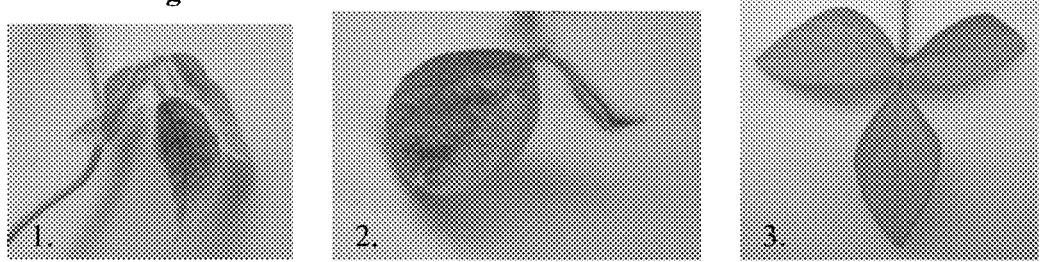
Figure 13A:
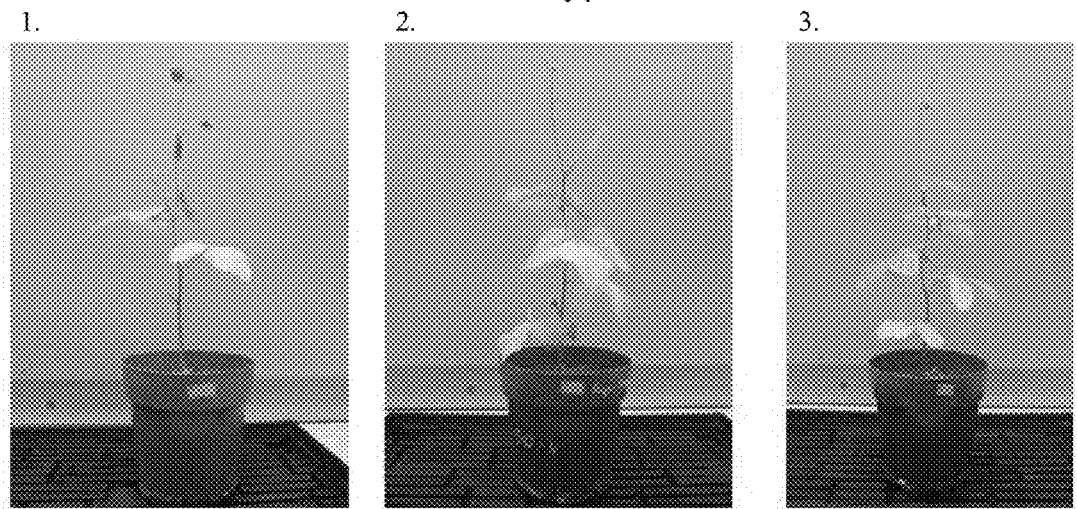
FIG. 13 (A-E) shows reduced disease symptoms in plants inoculated with gibberellin-deficient rhizobacteria compared to plants inoculated with gibberellin-sufficient rhizobacteria. Whole plants (A-B) and the 3rd-5th trifoliates of the plants (C-E) were photographed 38 days after exposure to *F. virguliforme*. Plants were 70 days old. The 4th trifoliate was completely absent (had fallen off) on one plant inoculated with wild-type (gibberellin-sufficient) rhizobacteria. Three replicates of each are shown (labeled 1-3).
Figure 13B:
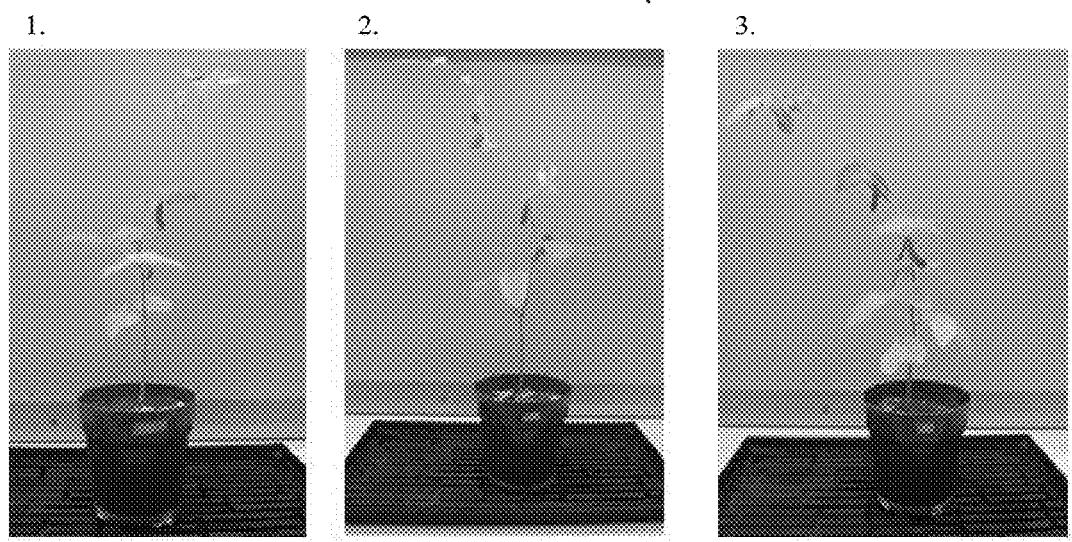
Figure 13C:
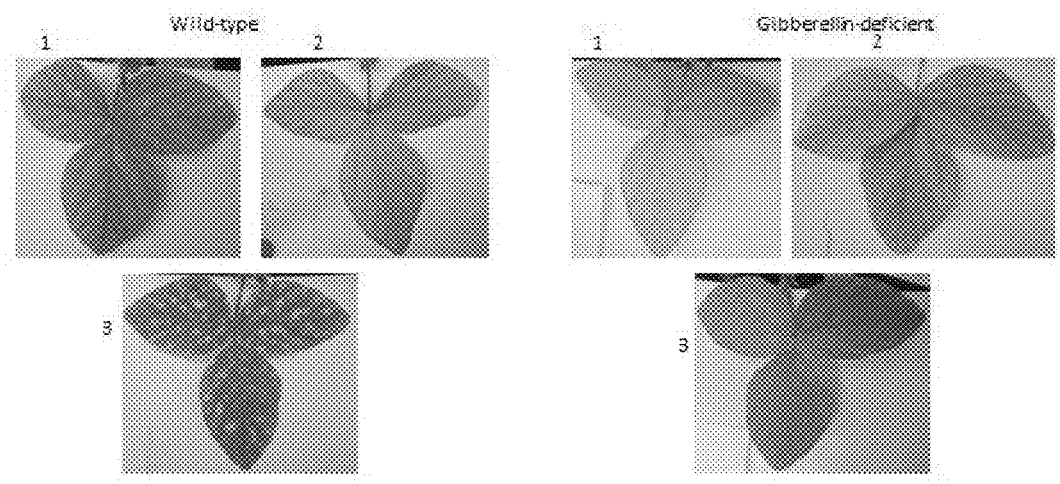
Figure 13D:
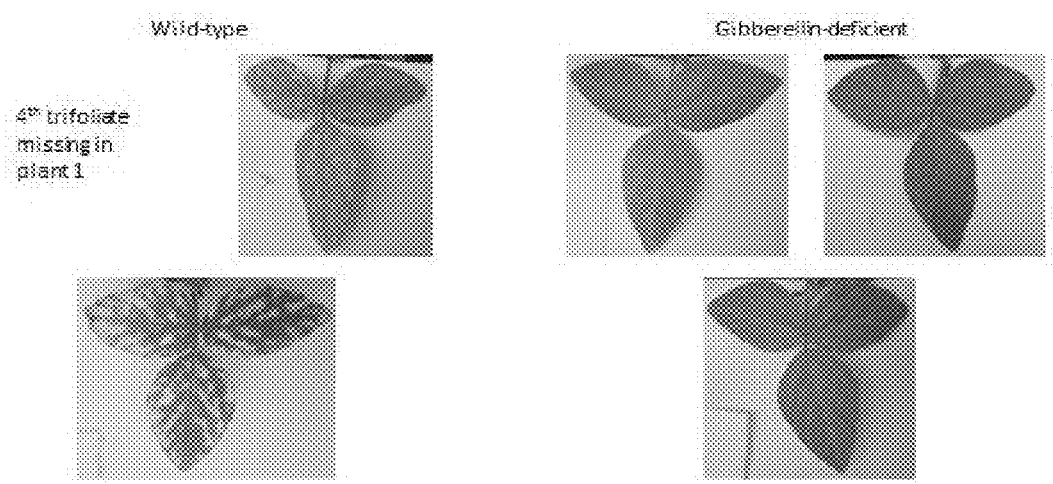
Figure 13E:
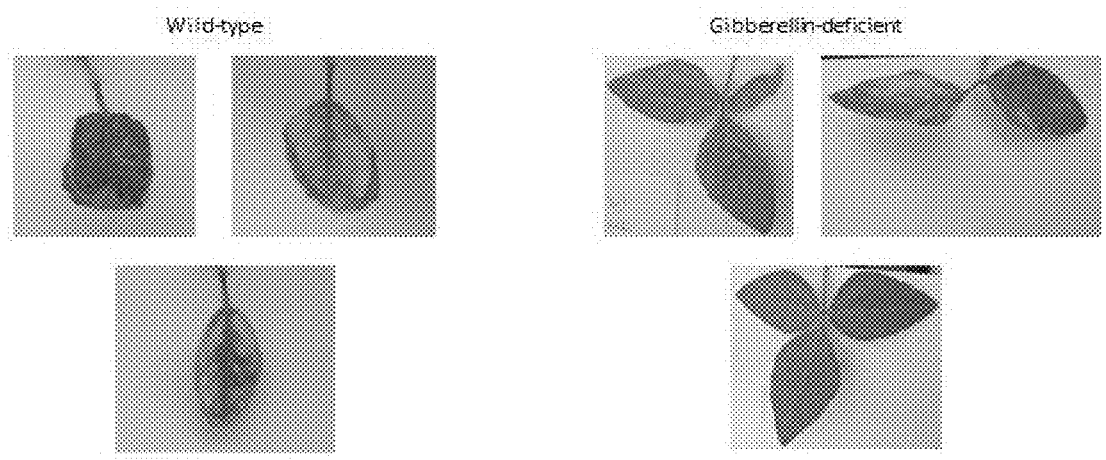
Figure 14A:
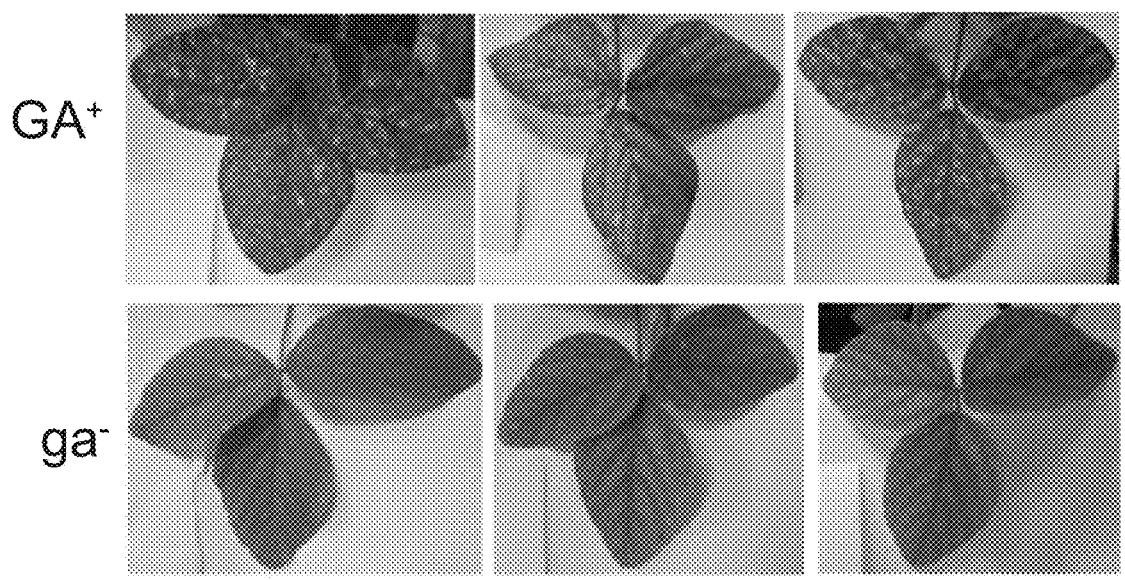
FIG. 14 (A-B) shows the effect of nodulation with gibberellin deficient (ga−) versus sufficient (GA+) strains of *B. japonicum* on sudden death syndrome (SDS) disease caused by *F. virguliforme*, which infects via the (nodulated) roots. Disease was observed in each trifoliate 11 weeks post-infection. (A) shows leaves from the 3rd-trifoliates. (B) shows quantification of SDS disease symptoms (leaf discoloration).
Figure 14B:
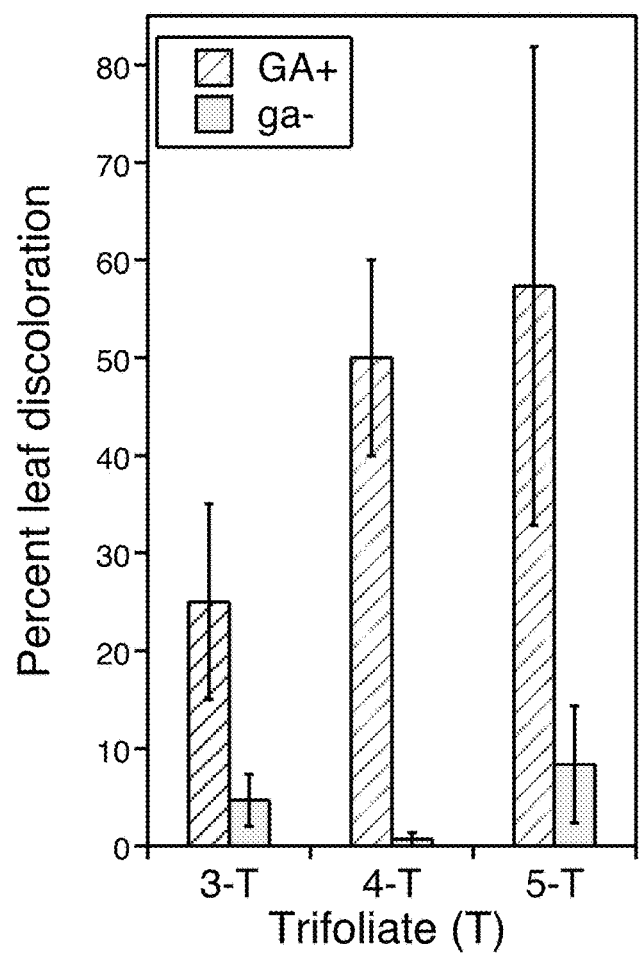

Plants inoculated with the gibberellin-deficient strain of *B. japonicum* do not exhibit any significant change in their growth and development relative to those inoculated with the gibberellin-sufficient USDA110 strain (see FIG. 8). This indicates that gibberellin-deficient rhizobacteria are able to fix nitrogen, with the decrease in average nodule size compensated for by increased numbers of nodules.

Flowering plants inoculated with gibberellin-deficient *B. japonicum* showed significantly less leaf discoloration at all points between 13 and 77 days after exposure to *F. virguliforme* (FIGS. 9-14). These data demonstrate that the plants inoculated with the gibberellin-deficient rhizobacteria were more resistant to disease than the plants inoculated with gibberellin-sufficient (i.e. wild-type) rhizobacteria.

What is claimed is:

1. A method for increasing pathogen resistance and/or plant growth of a nodulating plant, comprising:

providing to said nodulating plant a rhizobacteria, which has been modified to exhibit reduced or eliminated gibberellin production, so that pathogen resistance and/or plant growth is increased compared to plants provided with wild-type rhizobacteria.

2. The method of claim 1, further comprising modifying said rhizobacteria, wherein said modifying comprises knocking down or knocking out the all or part of the gibberellin locus in said rhizobacteria.

3. The method of claim 1, wherein said nodulating plant is *Glycine max, Phaseolus, Pisum sativum, Cicer arietinum, Medicago sativa, Arachis hypogaea, Ceratonia siliqua*, or *Glycyrrhiza glabra.*

4. The method of claim 1 wherein said increased pathogen resistance comprises a decrease in leaf discoloration.

5. The method of claim 4 wherein said decrease in leaf discoloration is at least 10%, compared to plants provided with wild-type rhizobacteria.

6. The method of claim 1 wherein said pathogen is *F. virguliforme.*

7. The method of claim 1 wherein said increased plant growth is increased plant height, increased plant biomass, and/or increased plant yield.

8. A method for increasing resistance to sudden death syndrome (SDS) in soybean, comprising:

providing to a soybean plant, or a seed or part thereof, a modified *B. japonicum* bacteria, wherein said modified *B. japonicum* comprises an interruption or excision of all or part of the endogenous gibberellin locus of said bacteria; and allowing nodulation of said soybean plant by said modified *B. japonicum* wherein said plant has increased resistance to SDS after nodulation with said modified *B. japonicum* compared to a plant nodulated with un-modified *B. japonicum.*

9. The method of claim 8 wherein said plant has at least 10% leaf discoloration compared to a plant nodulated with un-modified *B. japonicum.*

10. A method for increasing growth of a nodulating plant, comprising:

providing to a nodulating plant, or a seed or part thereof, a modified *B. japonicum* bacteria, wherein said modified *B. japonicum* comprises an interruption or excision of all or part of the endogenous gibberellin locus of said bacteria; and allowing nodulation of said nodulating plant by said modified *B. japonicum* wherein said nodulating plant has increased growth after nodulation with said modified *B. japonicum* compared to a plant nodulated with un-modified *B. japonicum.*

* * * * *